United States Patent [19]

Weber et al.

[11] Patent Number: 5,698,552
[45] Date of Patent: Dec. 16, 1997

[54] HETRAZEPINOID AMIDES

[75] Inventors: Karl-Heinz Weber; Werner Stransky, both of Gau Algesheim; Ulrike Kufner-Muhl, Mainz; Hubert Heuer, Schwabenheim; Franz Birke, Ingelheim am Rhein; Wolf-Dietrich Bechtel, Appenheim, all of Germany

[73] Assignee: Boehringer Ingelheim KG, Ingelheim am Rhein, Germany

[21] Appl. No.: 453,038

[22] Filed: May 31, 1995

Related U.S. Application Data

[62] Division of Ser. No. 290,169, Aug. 15, 1994, abandoned, which is a continuation of Ser. No. 71,159, Jun. 2, 1993, abandoned, which is a continuation of Ser. No. 927,096, Aug. 7, 1992, abandoned, which is a continuation of Ser. No. 750,374, Aug. 27, 1991, abandoned.

[30] Foreign Application Priority Data

Aug. 30, 1990 [DE] Germany ............... 40 27 470.5

[51] Int. Cl.⁶ .............. A61K 31/55; C07D 495/14
[52] U.S. Cl. ........................... 514/219; 540/555
[58] Field of Search ........................ 540/555; 514/219

[56] References Cited

U.S. PATENT DOCUMENTS

| | | | |
|---|---|---|---|
| 4,621,083 | 11/1986 | Casals-Stenzel et al. | 514/220 |
| 4,900,729 | 2/1990 | Stransky et al. | 514/220 |
| 4,937,240 | 6/1990 | Moriwaki et al. | 514/212 |
| 4,968,794 | 11/1990 | Weber et al. | 540/560 |
| 5,104,543 | 4/1992 | Brandt et al. | 210/635 |

FOREIGN PATENT DOCUMENTS

| | | |
|---|---|---|
| 2012411 | 9/1990 | Canada. |
| 254245 | 1/1988 | European Pat. Off.. |
| 407955 | 1/1991 | European Pat. Off.. |

OTHER PUBLICATIONS

US patent application 821,640 (Weber et al.), filed 23, Jan. 1986 (now abandoned).
US patent application 005,992 (Stransky et al.), filed 21 Jan. 1987 (now abandoned).
US patent application 076,515 (Weber et al.), filed 22 Jul. 1987 (now abandoned).
US patent application 346,862 (Heuer et al.), filed 3 May 1989 (now abandoned).
US patent application 348,364 (Heuer et al.), filed 8 May 1989 (now abandoned).
US patent application 433,075 (Weber et al.), filed 6 Nov. 1989 (now abandoned).
US patent application 552,712 (Weber et al.), filed 12 Jul. 1990 (now abandoned).

Harreus et al., *Chemical Abstracts*, 108:186776j (1988).

Weber et al., *Chemical Abstracts*, 113:191406w (1990).

*Primary Examiner*—Philip I. Datlow
*Attorney, Agent, or Firm*—Robert P. Raymond; Alan R. Stempel; Mary-Ellen Devlin

[57] ABSTRACT

The present invention relates to thienodiazepines of formula Ib:

wherein U, V, $R_5$, $R_6$ and $R_7$ are as defined herein. This invention also relates to processes for preparing these thienodiazepines and their use in pharmaceutical compositions with PAF-antagonistic activity.

4 Claims, No Drawings

HETRAZEPINOID AMIDES

This is a division of application Ser. No. 08/290,169, filed Aug. 15, 1994, now abandoned which is a continuation of application Ser. No. 08/071,159, filed Jun. 2, 1993 (abandoned), which is a continuation of application Ser. No. 07/927,096, filed Aug. 7, 1992 (abandoned), which is a continuation of application Ser. No. 07/750,374 filed Aug. 27, 1991 (abandoned).

The present invention relates to new hetrazepinoid amides, processes for their preparation and their use as pharmaceutical compositions having a PAF-antagonistic activity.

Substituted thienodiazepines having a PAF-antagonist activity are known from numerous publications and patent applications, e.g. from European Patent Applications 176 927, 194 416, 254 245, 230 942, 341 558, 341 559 and 368 175.

Surprisingly, it has been found that acid amides of a defined structure have improved pharmacological properties.

The new hetrazepines correspond to general formula I

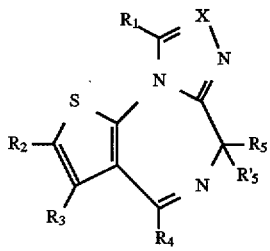

wherein $R_1$ represents hydrogen, halogen, a branched or unbranched $C_{1-4}$-alkyl group, preferably methyl, which may optionally be substituted by hydroxy or halogen, a cyclopropyl group, a cyclobutyl group, a cyclopentyl group, a branched or unbranched $C_{1-4}$-alkoxy group, preferably methoxy, halogen, preferably chlorine or bromine;

$R_2$ represents the group —Z—$R_a$

Z represents a branched or unbranched alkyl, alkenyl or alkynyl group having n carbon atoms, whilst Z may optionally be additionally substituted by an aryl group or additionally by $R_a$;

n represents one of the numbers 0, 1, 2, 3, 4, 5, 6, 7, 8, 9 or 10, whilst when Z represents an alkenyl or alkynyl group, n is >1 and preferably represents 2, 3 and 4;

$R_3$ represents hydrogen or methyl or $R_2$ and $R_3$ together represent a group of general formula

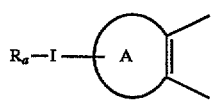

wherein

A represents a fused mono-unsaturated 5-, 6- or 7-membered carbocyclic ring,

I represents a branched or unbranched alkyl, alkenyl or alkynyl group having m carbon atoms;

m represents 0, 1, 2, 3, 4, 5 or 6, preferably 0;

$R_a$ represents a group of general formula

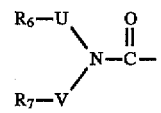

wherein

U and V independently of each other, being identical or different, may represent a single bond, a branched or unbranched $C_{1-6}$, preferably $C_{1-3}$-alkyl group, a $C_{2-6}$, preferably $C_{2-3}$-alkenyl group, or a $C_{2-6}$, preferably $C_{3-4}$-alkynyl group, $R_6$ represents hydrogen or a group of the formula

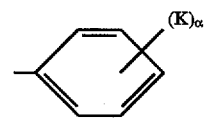

or optionally substituted $C_{3-6}$-cycloalkyl or $C_{5-6}$-cycloalkenyl;

$R_7$ represents a group of formula

or

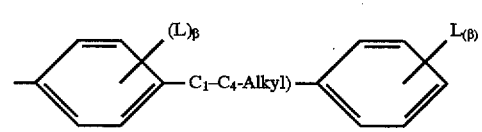

or optionally substituted $C_{3-6}$-cycloalkyl or $C_{5-6}$-cycloalkenyl;

K and L independently of each other represent hydrogen, halogen, hydroxy, nitro, cyano, trifluoromethyl, branched or unbranched $C_{1-8}$, preferably $C_{1-4}$-alkyl, optionally substituted by halogen or hydroxy, optionally substituted $C_{3-6}$-cycloalkyl, optionally substituted branched or unbranched $C_{1-8}$, preferably $C_{1-4}$-alkoxy, a group of formula

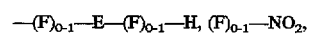

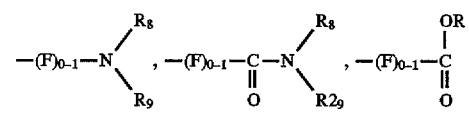

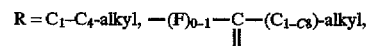

preferably $C_1$–$C_4$-alkyl, wherein F represents a branched or unbranched $C_{1-4}$-alkyl, preferably $C_{1-2}$-alkyl group,

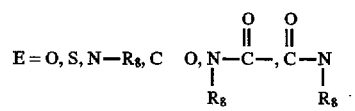

-continued

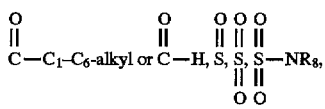

F represents a branched or unbranched, optionally substituted $C_{1-8}$-alkyl, preferably $C_{1-4}$-alkyl, an optionally substituted $C_{2-8}$-, preferably $C_{2-4}$-alkenyl, an optionally substituted $C_{2-8}$-alkynyl, preferably $C_{2-4}$-alkynyl;

wherein $R_8$ and $R_9$, which may be identical or different, may represent hydrogen, phenyl, substituted phenyl, a branched or unbranched alkyl, alkenyl or alkynyl group having 1 to 6 carbon atoms, preferably 1 to 4 carbon atoms, and optionally substituted by halogen, hydroxy, nitro, amino, substituted amino, $C_{3-6}$-cycloalkyl, preferably cyclopropyl, $C_{1-4}$-alkoxy, preferably methoxy;

$P_8$ or $R_9$ may represent a saturated or unsaturated 5-, 6- or 7-membered heterocyclic ring linked via a carbon and optionally mono- or polysubstituted by branched or unbranched $C_{1-4}$-alkyl, an optionally substituted $C_{3-7}$-cycloalkyl, an optionally substituted cycloalkenyl group; or $R_8$ and $R_9$, if structurally possible, together with the nitrogen atom represent a saturated or unsaturated 5-, 6- or 7-ring optionally mono or polysubstituted by branched or unbranched $C_{1-4}$-alkyl groups, and possibly containing nitrogen, oxygen or sulphur as further heteroatoms, whilst each additional nitrogen atom may be substituted by a branched or unbranched $C_{1-4}$-alkyl group, preferably methyl;

α and β independently of each other may represent one of the numbers 1, 2, 3, 4 or 5, whilst if α or β is greater than 1 all the Ks and Ls may be identical, partially identical or different;

$R_6$ may represent a pyridyl, thiophene or furan group 5- or 6-membered heterocyclic ring containing nitrogen, oxygen or sulfur as heteroatoms—preferably a pyridyl, thiophene or furan group—which may optionally be mono or polysubstituted, by identical or different substituents, by halogen, $C_{1-4}$-alkyl, $C_{1-4}$-haloalkyl, preferably $CF_3$, nitro, $NR_8R_9$ or S—$C_{1-4}$-alkyl, $R_7$ may represent a C-linked saturated or unsaturated 5- or 6-membered heterocyclic ring containing nitrogen, oxygen or sulphur as heteroatoms—preferably a pyridyl, thiophene or furan group—which may optionally be mono or polysubstituted, identically or differently, by halogen, $C_{1-4}$-alkyl, $C_{1-4}$-haloalkyl, preferably $CF_3$, nitro, $NR_8R_9$ or S—$C_{1-4}$-alkyl, $R_4$ represents phenyl, whilst the phenyl ring may be mono or polysubstituted, preferably in the 2-position, by methyl, preferably halogen, especially chlorine or bromine, nitro, alkoxy, preferably methoxy and/or trifluoromethyl, or $R_4$ may represent pyridyl or thienyl which may optionally be substituted by $C_{1-4}$-alkyl or halogen;

$R_5$ represents hydrogen, methyl, trifluoromethyl, cyclopropyl, hydroxymethyl;

$R'_5$ represents hydrogen or methyl;

X represents nitrogen, C—H, C—$CH_3$;

optionally in the form of the racemates, the enantiomers, the diastereomers and mixtures thereof and optionally the physiologically acceptable acid addition salts thereof. [Carbon atoms which embody a centre of asymmetry are hereinafter marked by an asterisk. In the Examples, racemates are designated by the prefix (+/−)].

Preferred compounds are compounds of general formula Ia

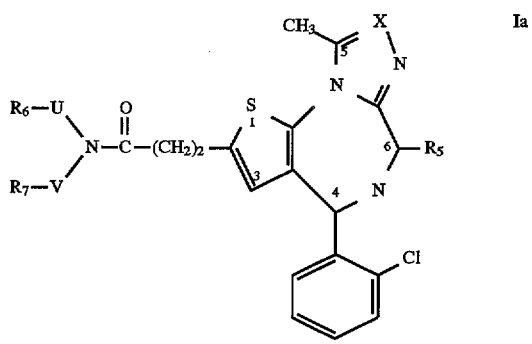

wherein

U represents a single bond, a branched or unbranched $C_{1-4}$-alkyl, $C_3$ or $C_4$-alkenyl, $C_3$ or $C_4$-alkynyl group;

V represents a single bond, a branched or unbranched $C_{1-4}$-alkyl group;

$R_5$ represents hydrogen or methyl;

$R_6$ represents a group of formula

as hereinbefore defined, or cyclopropyl, cyclopentyl, cyclohexyl, or preferably hydrogen;

$R_7$ represents a group of formula

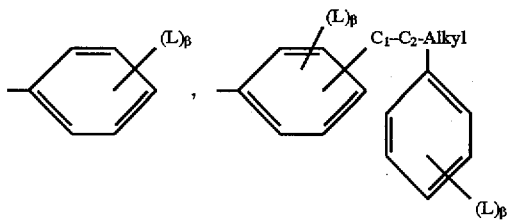

as hereinbefore defined, a pyridinyl, a thien-2-yl or a furan-2-yl group and

X may represent nitrogen or CH.

Preferred compounds in the form of the racemates thereof, particularly in the form of their optically active isomers of general formula I having a fused carbocyclic ring are

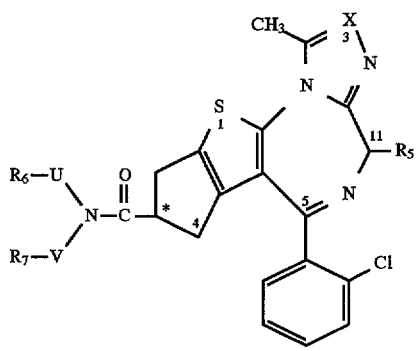

and

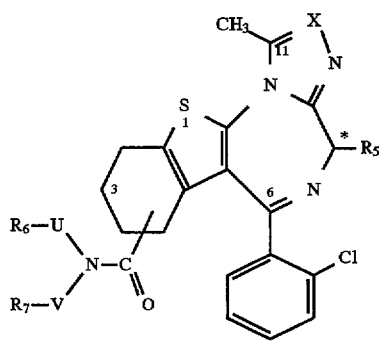

wherein

U represents a single bond, branched or unbranched $C_{1-4}$-alkyl, $C_3$ or $C_4$-alkenyl, $C_3$ or $C_4$-alkynyl;

V represents a single bond, branched or unbranched $C_{1-4}$-alkyl;

$R_5$ represents hydrogen or methyl;

$R_6$ represents a group of formula

as hereinbefore defined, or cyclopropyl, cyclopentyl, cyclohexyl, or preferably hydrogen;

$R_7$ represents a group of formula

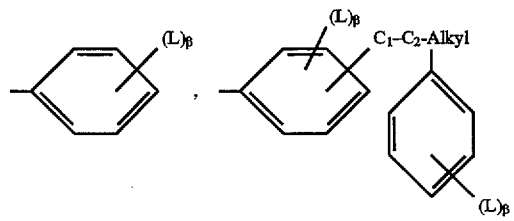

as hereinbefore defined, or a pyridinyl, thien-2-yl or furan-2-yl group and

X represents nitrogen or CH.

Particularly preferred compounds are those of general formula Ia, Ib and Ic wherein X represents nitrogen, U preferably represents a single bond or $C_{1-4}$-alkyl, preferably propyl, allyl, propargyl;

V represents $C_{1-4}$-alkyl, preferably methylene;

$R_6$ preferably represents hydrogen, cyclopropyl or

$R_7$ represents

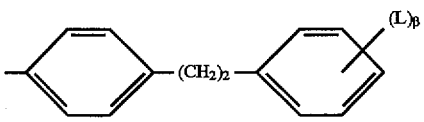

K and L independently of each other represent hydrogen, optionally halogen- or hydroxy-substituted $C_{1-4}$-alkyl, $C_{2-4}$-alkynyl, $C_{2-4}$-alkenyl, nitro, cyano, hydroxy, $C_{1-4}$-alkoxy, $C_{1-4}$-alkoxy-$C_{1-4}$-alkyl, $C_{1-4}$-alkylsulphonyl, halogen, $C_{1-5}$-hydroxyalkyl-sulphonyl, $COOC_{1-4}$-alkyl, $COOC_{1-4}$-alkylphenyl, cyclopropyl, SH, S—$C_{1-4}$-alkyl;

α represents 1, 2 or 3, preferably 1;

β represents 1, 2 or 3, preferably 1; preferably $(K)_α$ hydrogen, $CF_3$ or halogen and $(L)_β$ preferably represents hydrogen, F, Cl, Br, methyl, trifluoromethyl, $CH_3O_2S$, hydroxy, whilst $(K)_α$ and $(L)_β$ are preferably arranged in the 4-position of the phenyl ring.

The S(−)-isomers of general formula Ib when $R_5$ represents hydrogen are also particularly preferred.

The mixtures of optically isomeric compounds which may occur during synthesis may be resolved into the individual optical isomers by forming diastereomers and subsequently separating them by methods known per se, e.g. by crystallisation or by chromatographic or enzymatic methods of separation.

The invention relates to the individual isomers, the mixtures thereof and optionally the corresponding physiologically suitable acid addition salts with organic or inorganic acids. Salts with hydrochloric, hydrobromic, sulphuric, phosphoric, methanesulphonic, ethanesulphonic, toluenesulphonic, benzenesulphonic, lactic, malonic, succinic, maleic, fumaric, malic, tartaric, citric or benzoic acid are preferred.

Unless otherwise stated, the general definitions are used as follows:

Alkyl generally represents a branched or unbranched hydrocarbon group having 1 to 6 carbon atoms which may optionally be substituted by a halogen atom or several halogen atoms, preferably fluorine, which may be identical or different, lower alkyl groups for a branched or unbranched hydrocarbon group having 1 to about 4 carbon atoms being preferred.

Unless otherwise stated, the preferred alkyl groups (including those which are parts of other groups) are methyl, ethyl, propyl, isopropyl, n-propyl, n-butyl, isobutyl, sec.-butyl and tert.-butyl.

Alkenyl generally represents a straight-chained or branched $C_{2-6}$-hydrocarbon group and having one or more, preferably one double bond, which may optionally be substituted by a halogen atom or several halogen atoms, preferably fluorine, which may be identical or different. A lower alkenyl group having 2 to about 4 carbon atoms and one double bond is preferred. Examples include vinyl, allyl, propenyl, isopropenyl, pentenyl and isopentenyl.

Alkynyl generally denotes a straight-chained or branched $C_{2-6}$-hydrocarbon group having one or more, preferably one triple bond, which may optionally be substituted. A lower alkynyl group having 2 to 4 carbon atoms and one or two triple bonds and optionally substituted by one or more halogen atoms which may be identical or different, is preferred. Examples include ethynyl, propargyl and 2-butynyl.

Cycloalkyl generally denotes a saturated or unsaturated cyclic hydrocarbon group having 3 to 6 carbon atoms, which may optionally be substituted by one or more halogen atoms, a hydroxy group or an alkyl group, preferably methyl, the substituents being identical or different. Examples include cyclopropyl, cyclobutyl, cyclopentyl, cyclopentenyl, cyclohexyl, cyclohexenyl. Phenyl groups may be substituted, for example, by one or more lower alkyl, alkoxy, nitro or amino groups and/or one or more halogen atoms (the substituents being identical or different).

A substituted phenyl group may, for example, also carry one or more of the following substituents: $C_{1-6}$-alkyl, $C_{1-6}$-alkoxy, halogen, amino, alkylamino, dialkylamino, $CF_3$, $D_{3-6}$-cycloalkyl, cyano, $NO_2$, COH, COOH, $COOC_{1-4}$-alkyl, cyclopropyl, hydroxy, SH, S—$C_{1-4}$-alkyl and hydroxymethyl.

Examples of substituted phenyl groups are as follows: 3-chlorophenyl, 4-chlorophenyl, 3-bromophenyl, 4-bromophenyl, 4-fluorophenyl, 2-chlorophenyl, 2-bromophenyl, 3-fluorophenyl, 2,3-dichlorophenyl, 2-methylphenyl, 4-methylphenyl, 3-ethylphenyl, 4-propylphenyl, 4-isopropylphenyl, 4-butylphenyl, 4-tert-butylphenyl, 4-iso-butylphenyl, 4-pentylphenyl, 2,4-dimethylphenyl, 2-trifluoromethylphenyl, 3-trifluoromethylphenyl, 4-trifluoromethylphenyl, 2-methoxyphenyl, 4-methoxyphenyl, 3-ethoxyphenyl, 2-propoxyphenyl, 4-butoxyphenyl, 2,4-dimethoxyphenyl, 3,4,5-trimethoxy-phenyl.

Alkoxy generally represents a straight-chained or branched $C_{1-18}$-hydrocarbon group bound via an oxygen atom. Lower alkoxy having from 1 to about 6 carbon atoms is preferred. An alkoxy group having 1 to 4 carbon atoms is particularly preferred. Examples include methoxy, ethoxy, propoxy, isopropoxy, butoxy, isobutoxy, tert.-butoxy, pentoxy, isopentoxy, hexoxy, isohexoxy, heptoxy, isoheptoxy, octoxy or isooctoxy.

Unless otherwise stated, the number of carbon atoms specified relates to the length of the alkyl, alkenyl or alkynyl chain.

Fused 6-membered rings A, wherein the side chain —I—$R_a$ is substituted in 3- or 4-position of the hetrazepine or fused 5-membered rings A wherein the side chain —Z—$R_a$ is substituted in the 3-position of the hetrazepine are particularly preferred.

The definition of a heterocyclic group for the purposes of this invention generally denotes a 5- to 7-membered ring which may contain oxygen, sulphur and/or nitrogen as heteroatoms and onto which another aromatic ring, preferably phenyl, may be fused. 5- and 6-membered aromatic rings containing an oxygen, a sulphur and/or up to two nitrogen atoms are preferred, e.g. thienyl, furyl, pyridyl, pyrimidyl, pyrazinyl, quinolyl, isoquinolyl, qainazolyl, quinoxalyl, benzoxazolyl, isoxazolyl, imidazolyl, benzimidazolyl, pyrazolyl and indolyl.

The heterocyclic group may be substituted by halogen, hydroxy and/or branched or unbranched $C_{1-4}$-alkyl.

Examples of optionally substituted, saturated or unsaturated heterocyclic 5-, 6- or 7-membered rings or heteroaryl groups are:

pyrrole, pyrroline, pyrrolidine, 2-methylpyrrolidine, 3-methylpyrrolidine, piperidine (optionally mono- or polysubstituted by $C_{1-4}$-alkyl), piperazine, N-methylpiperazine, N-ethylpiperazine, N-n-propylpiperazine, N-benzylpiperazine, morpholine, thiomorpholine, imidazole, imidazoline, imidazolidine, triazole, pyrazole, pyrazoline, pyrazolidine, triazine, 1,2,3,4-tetrazine, 1,2,3,5-tetrazine, 1,2,4,5-tetrazine, whilst the above-mentioned heterocyclic groups may be substituted by $C_{1-4}$-alkyl, preferably methyl;

Examples of heterocyclic groups which may be linked via a carbon atom include thiophene, 2-methylthiophene, furan, 2-methyltetrahydrofuran, tetra-hydrofuran, 2-hydroxymethylfuran, α-pyran, γ-pyran, 1,3-dioxolane, 1,2-oxathiolane, 1,2-oxathiepan, tetrahydro-pyran, thiolane, 1,3-dithiane, 1,3-dithiolane, 1,3-dithiolene, whilst the heterocyclic group may be substituted by $C_{1-4}$-alkyl, $C_{1-4}$-alkoxy or halogen.

As is known, PAF (platelet activating factor) is the phospholipid acetyl-glyceryl-ether-phosphoryl-choline (AGEPC), which is known as a potent lipid mediator released by proinflammatory animal and human cells. Such cells chiefly include basophilic and neutrophilic granulocytes, macrophages (from blood and tissue) and platelets, which participate in inflammation reactions.

In pharmacological experiments, PAF shows bronchoconstriction, a reduction in blood pressure, inducement of platelet aggregation and a proinflammatory action.

These experimentally detectable actions of PAF directly or indirectly indicate possible functions of this mediator in anaphylaxis, in the pathophysiology of bronchial asthma and generally in inflammation.

PAF antagonists are required on the one hand to clarify further pathophysiological functions of this mediator in animals and humans and on the other hand to treat pathological conditions and diseases in which PAF participates. Examples of the indications of a PAF antagonist are inflammation processes of the tracheobronchial tree (acute and chronic bronchitis, bronchial asthma) or of the kidney (glomerulonephritis), of the joints (rheumatic diseases), anaphylactic states, allergies and inflammations in the region of the mucosa and skin (e.g. psoriasis) and shock states caused by sepsis, endotoxins or burns. Other important indications for a PAF antagonist are lesions and inflammations in the region of the gastric and intestinal mucosa, such as e.g. gastritis, peptic ulcers in general, but in particular gastric ulcers and duodenal ulcers.

The compounds according to the invention are furthermore suitable for the treatment of the following diagnoses: Obstructive pulmonary diseases, such as e.g. bronchial hyperreactivity, inflammatory diseases of the pulmonary tract, such as e.g. chronic bronchitis;

cardiovascular diseases, such as e.g. polytrauma, anaphylaxis, arteriosclerosis, inflammatory intestinal diseases, EPH-gestosis (oedema-proteinuria-hypertension), diseases of the extracorporeal circulation, ischaemic diseases, inflammatory and immunological diseases, immunomodulation for transplants of foreign tissues, immunomodulation for leukaemia, the spread of metastases, e.g. with bronchial neoplasia, and diseases of the CNS, such as e.g. migraine, agoraphobia (panic disorder), and the compounds according to the invention furthermore prove to be cyto- and organoprotective, e.g. for neuroprotection, e.g. in cases of cirrhosis of the liver, DIC (disseminated intravasal coagulation);

side effects of medicament therapy, e.g. anaphylactoid circulatory reactions, contrast medium incidents, side effects of tumour therapy; haemolytic uremic syndrome;

incompatibilities with blood transfusions; fulminant liver failure ($CCl_4$ intoxication)

Amanita phalloides intoxication (death-head intoxication); primary biliary cirrhosis, symptoms of parasitic diseases (e.g. worm diseases); autoimmune diseases.

The following indications are furthermore of interest: Immune function in cases of AIDS, diabetes, juvenile diabetes, diabetic retinopathy, polytraumatic shock, haemorrhagic shock, CNS: ischaemia, multiple sclerosis, migraine, colitis ulcerosa, Crohn's disease, psoriasis, high pulmonary pressure and chronic ischaemic cardiac insufficiency. PAF antagonists of the general formula I are suitable for the treatment of pathological changes in blood gases, such as, for example, respiratory acidosis, metabolic alkalosis. PAF antagonists can be used in combination with anticholinergics to improve the blood gas values in cases of phosphoric acid ester intoxication. It is known that PAF antagonists by themselves—or in combination with immunosupressant compounds (e.g. cyclosporins)—can be used for the treatment of autoimmune diseases and in transplant cases.

The use of PAF antagonists in combination with antihistamines is furthermore proposed. With regard to the definition of antihistamines, the content of European Patent Application 345 731 and EP 35749 (epinastine) is referred to. Particularly preferred is a combination of epinastine and S(−)-3-((4-trifluoromethylbenzyl)propylaminocarbonyl)-5-(2-chlorophenyl) -10-methyl-7H-cyclopenta[4,5]thieno-[3, 2-f]-[1,2,4]triazolo[4,3-a][1,4]diazepine (Example 18). It is furthermore known that PAF antagonists in combination with $\beta_2$-mimetics can be used for the treatment of bronchial asthma. Combination of PAF antagonists with TNF is also advantageous. PAF-associated interaction with tissue hormone (autocoid hormones), lymphokines and other mediators.

Combinations of compounds of general formula I with prostacyclines, for example, are also of interest, e.g. for preserving organs before transplantation. Prostacycline is a naturally occurring platelet aggregation inhibitor, but is metabolised very rapidly in the body. For this reason, stable derivatives or analogues of prostacycline have already been synthesised and investigated in clinical trials for their suitability as substitutes for prostacycline. These include, for example, Ataprost, Beraprost, Cicaprost, Ciprosten, Eptalprost, Iloprost, Nileprost, 7-oxo-prostaglandine $I_2$, Taprosten, TEI-8166 A and TRY-2000.

The new hetrazepines are very potent PAF antagonists and are superior to other known diazepinoid PAF antagonists in the following criteria:

there is total dissociation between the PAF antagonism and the effects mediated to the benzodiazepine receptor;

superior bonding affinity with the PAF receptor on washed human platelets, and they exhibit a greater inhibition of PAF-induced platelet aggregation;

they moreover inhibit, in a superior manner, bronchoconstriction induced by PAF (30 ng/kg×min) after oral and parenteral administration to guinea pigs, in combination with a very long action time (more than 15 h after oral administration to guinea pigs).

The following table shows some of the selected compounds with the associated values for inhibition of PAF-induced platelet aggregation.

| Example | PAF-induced platelet aggregation [μmol] |
| --- | --- |
| 2 | 0.049 |
| 6 | 0.023 |
| 7 | 0.084 |
| 10 | 0.037 |

Method 200 ml samples of blood were taken from a nonobstructed vein, with the aid of a plastic syringe containing 3.8% sodium citrate solution, from healthy male and female donors aged from 18 to 35 years who had not taken any medicaments (aspirin or other non-steroid anti-inflammatories) for several days before the blood withdrawal. The ratio of sodium citrate solution:blood was 1:9. The citrated blood was centrifuged in plastic tubes at 150 ×g (=1,200 rpm) at room temperature for 20 min (Heraeus Christ bench centrifuge 124).

The platelet aggregation was measured in vitro by the method of Born and Cross (1963), an aggregation inducer (PAF) being added to the TRP, while stirring constantly. For the measurement, 0.8 ml TRP and 0.2 ml modified Tyrode's solution (see below) were introduced into 1 ml plastic cells, each of which contained a small metal pin (stirrer, 1,000 rpm). The test substance was added in a volume of 10 μl for 2 to 3 min before inducing the aggregation. Either DMSO and water or a dilute HCl solution was used as the solvent. The control batches contained the corresponding volume of these solvents. After recording the initial absorption (2–3 min), aggregation was induced. PAF (5 ×10$^{-8}$M; Bachem Feinchemikalien) was introduced into the cell in a volume of 10 μl.

The modified Tyrode's solution had the following composition: 136.9 mM NaCl; 2.68 mM KCl; 0.5 mM $MgCl_2$; 1.8 mM $CaCl_2$; 0.42 mM $NaH_2PO_4$; 5.55 mM glucose and 11.9 mM $NaHCO_3$.

To evaluate substance effects, the maximum of the first aggregation wave was used. The maximum absorption induced by the aggregation inducer (=maximum aggregation=100%) was simultaneously run in a parallel batch (in the 2nd channel of the aggregometer) to each test batch and used as the 100% value. The aggregation value achieved under the action of the test substance was quoted as % of the control value (batch).

Concentration/effect curves with a random sample size of in each case n=4 were plotted with the aid of this method and $IC_{50}$ values (concentration at 50% aggregation inhibition) were calculated.

The new compounds may be obtained in the usual way from the corresponding 2-carboxylic acids of general formula

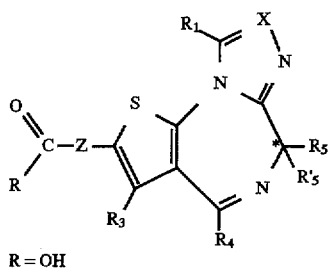

IIa

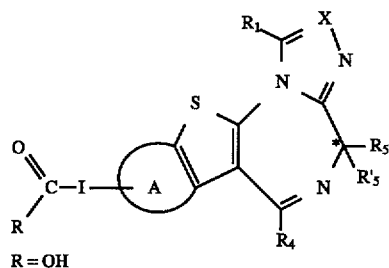

IIb

R = OH wherein the groups R are defined as hereinbefore, e.g.

a) by reaction with a corresponding amine in the presence of a carbodiimide or carbonyldiimidazole, b) by converting the free acid into an acid halide or acid anhydride and subsequently reacting with a corresponding amine.

The reaction of the free acid with the amine is carried out in the presence of a carbodiimide for example cyclohexylcarbodiimide, optionally with the aid of hydroxybenzotriazole or using carbonyldiimidazole in an inert solvent such as dimethylformamide, tetrahydrofuran, dioxane etc., at temperatures between 0° C. and the boiling point of the reaction mixture.

When the amine is reacted with an acid halide or acid anhydride, the amine is reacted with the acid halide or acid anhydride in an inert solvent, such as dimethylformamide, tetrahydrofuran, dioxane or a suitable hydrocarbon such as benzene or toluene at temperatures between ambient temperature and the boiling point of the reaction mixture, optionally with the addition of an acid-binding agent such as sodium carbonate, sodium bicarbonate or a tertiary organic base, e.g. pyridine or triethylamine.

Acid halide or acid anhydride is obtained from the free acid in the usual way, e.g. by reacting the acid with a thionylhalide or phosphorusoxyhalide or by reacting an alkali metal salt of the acid with acetyl chloride or chloroformic acid chloride.

The compounds according to the invention can be prepared analogously according to the prior art.

The suitable carboxylic acid esters of general formula IIa/IIb, R=OC$_{1-4}$-alkyl, are synthesised in accordance with European Patent 194 416 and European Patent Applications 230 942 and 254 245, and may subsequently be saponified to form the carboxylic acid according to the following reactions.

Starting from the suitable substituted diazepinethiones of general formula IIIa or IIIb—wherein, in the case of IIIb, the optical activity may optionally be produced at the chiral centre of the carbocyclic 5- or 6-membered ring according to German Patent Application DE 39 09 012.4 or the corresponding European Patent Application, Application No. 90 104 890.0, or at the diazepine ring—

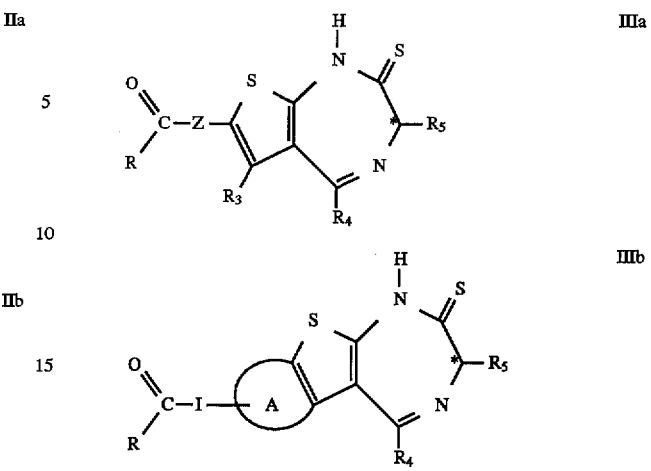

wherein R, R$_3$, R$_4$, R$_5$, A, I and Z are defined as in formula IIa and IIb hereinbefore, the carboxylic acid esters of general formulae IIa and IIb (R=alkoxy) are obtained as follows A) if X represents nitrogen a) by reacting with an acid hydrazide of general formula R$_1$ —CONHNH$_2$, b) or by converting with hydrazine into the corresponding hydrazino compound and subsequently reacting with an acid halide of general formula R$_1$—CO—Hal or with an orthoester of general formula R$_1$—C(OR')$_3$ wherein R' represents a lower alkyl group, or B) if X represents C—H or C-alkyl a) by reacting with an aminoalkyne of general formula R'$_1$—C≡C—CH$_2$—NH$_2$, wherein R'$_1$ represents hydrogen or a lower alkyl group or b) by reacting with an α-aminoaldehyde-alkylacetal or α-aminoketone-alkylketal of general formula

H$_2$NCH$_2$—CR$_1$(OR')$_2$ wherein R$_1$ represents hydrogen or a C$_{1-4}$-alkyl group and R' represents a lower alkyl group.

Subsequently, if desired, the compounds of type I wherein R$_1$=hydrogen may be reacted in the presence of a base with a halogenating agent, such as chlorine or bromine, to obtain a compound of general formula I wherein R$_1$ represents halogen, e.g. chlorine or bromine.

Subsequently, if desired, the halogen compound may be converted into a compound of general formula I wherein R$_1$=C$_{1-4}$-alkoxy by reacting with the corresponding alkoxide.

The reaction of the thione IIIa/IIIb with an acid hydrazide according to process a) is carried out in an inert organic solvent, e.g. dioxane, dimethylformamide, tetrahydrofuran or a suitable hydrocarbon, such as benzene or toluene, at temperatures between ambient temperature and the boiling point of the reaction mixture. The end products are isolated by known methods, e.g. crystallisation.

The reaction of the thione IIIa/IIIb with hydrazine according to process b) is carried out in inert organic solvents, such as tetrahydrofuran, dioxan, halogenated hydrocarbons such as methylene chloride, suitable hydrocarbons, at temperatures between ambient temperature and the boiling point of the reaction mixture.

The resulting hydrazine-1,4-diazepines may be isolated by conventional methods or used directly for further processing.

The further reaction with an acid halide or orthoester is carried out in an inert organic solvent, e.g. halogenated hydrocarbons or cyclic or aliphatic esters, but may also be carried out directly in the substance. The end product Ia is isolated by known methods such as crystallisation.

If the optical activity is not produced from synthesis precursors according to German Patent Application DE 39 09 012.4, the end compounds may also be resolved into their enantiomers by methods of separation known per se. This may also apply to suitable chiral acids.

EXAMPLE 1

4-(2-Chlorophenyl)-9-methyl-6H-thieno[3,2-f][1,2,4]-triazolo-[4,3-a][1,4]diazepino-2-(2-ethyl)-carboxylic acid propyl-(4-trifluoromethylbenzyl)amide

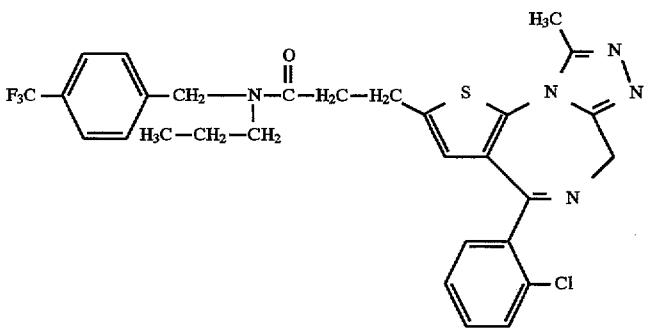

4.6 g (0.068 mol) of imidazole are dissolved in 50 ml of methylene chloride and 2 g (1.2 ml) of thionyl chloride are slowly added. Then, over a period of 10–15 minutes at 15° to 20° C., 6.5 g (0.017 mol) of 4-(2-chlorophenyl)-9-methyl-6H-thieno[3,2-f][1,4]diazepino-2-(2-ethyl)-carboxylic acid [W. D. Bechtel and K. H. Weber, J. Pharmac. Sci. 74 (1985) 1265] are added thereto and the mixture is stirred for a further 15–20 minutes. 3.6 g (0.017 mol) of N-propyl-(4-trifluoromethylbenzyl)-amine are added to the resulting imidazolide and the mixture is stirred for 1 hour. The reaction mixture is diluted with 100 ml of methylene chloride and extracted twice with 50 ml of water. From the dried methylene chloride phase, after evaporation, an oil is obtained which crystallises when ether is added.

Yield 5.8 g; m.p. 182°–183° C., $^1$H-NMR (CDCl$_3$): δ=7.62–7.14 (8H, m, aryl-H); 6.45, 6.39 (1H, 2s, thiophene-H); 4.92 (2H, s, CH$_2$-7-ring); 4.64, 4.56 (2H, 2s, N—CH$_2$-aryl); 3.42–3.06 (4H, m, CH$_2$-thiophene; N—CH$_2$CH$_2$CH$_3$); 2.74, 2.59 (2H, 2t, J=6 Hz, CH$_2$—C=O); 2.69 (3H, s, CH$_3$-triazole); 1.52 (2H, m, N—CH$_2$CH$_2$—CH$_3$); 0.87 (3H, m, N—CH$_2$CH$_2$CH$_3$).

The N-propyl-N(4-trifluoromethyl)benzylamine is prepared as follows:

10 g (0.057 mol) of 4-trifluoromethylbenzaldehyde are added dropwise to 3.8 g (0.065 mol) of propylamine in 100 ml of ethanol, with stirring and cooling with ice. The mixture is stirred for 1 hour at ambient temperature, cooled with ice again and 1.4 g (0.036 mol) of sodium borohydride are gradually added at 10° to 15° C. The mixture is then stirred for 30 minutes at ambient temperature and for 1 hour at 35°–40° C. A pH of 5 is adjusted using 2N hydrochloric acid and the alcohol is distilled off in vacuo. Dilute ammonia is added to the residue until a clearly alkaline reaction is obtained and the amine is extracted several times with ethyl acetate. After drying and evaporation, the residue is distilled in vacuo (Bp$_{0.15}$: 63° C.).

$^1$H-NMR (CDCl$_3$): δ=7.49 (4H, m, aryl-H); 3.84 (2H, 2s, N—CH$_2$-aryl); 2.59 (2H, t, J=6 Hz, N—CH$_2$CH$_2$—CH$_3$); 1.54 (2H, m, N—CH$_2$CH$_2$—CH$_3$); 1.46 (1H, s, broad, NH); 0.93 (3H, t, J=6 Hz, N—Ch$_2$CH$_2$—CH$_3$).

EXAMPLE 2

S(−)-3-(Benzylpropylaminocarbonyl)-5-(2-chlorophenyl)-10-methyl-7H-cyclopenta[4,5]thieno[3,2-f][1,2,4]-triazolo-[4,3-a][1,4]diazepine

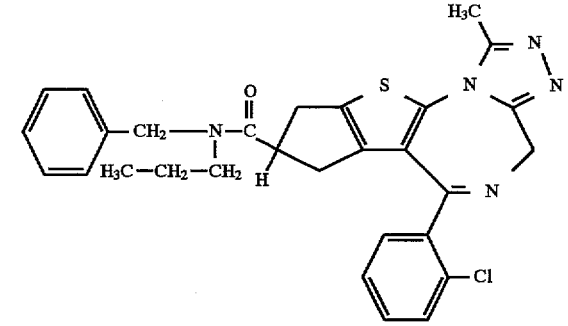

1.5 g (0.0038 mol) of S(−)-3-carboxy-5-(2-chlorophenyl)-10-methyl-7H-cyclopenta[4,5]thieno[3,2-f][1,2,4]-triazolo-[4,3-a][1,4]diazepine [German Patent Application 39 09 012.4 or European Patent Application No. 90 104 890.0] are dissolved or suspended in 20 ml of dimethylformamide and at 0 to 10° C. 0.6 g (0.004 mol) of N-propylbenzylamine, 0.61 g of hydroxybenzotriazole and 0.91 g of dicyclohexylcarbodiimide are added. The mixture is stirred for 8 hours at this temperature, left to stand overnight in a refrigerator and then the urea precipitated is removed by suction filtering. The filtrate is diluted with 50 ml of ethyl acetate and extracted with 20 ml of water, then dried, filtered and evaporated in vacuo. The residue is taken up in methylene chloride, washed with sodium bicarbonate solution, dried and evaporated once more. After filtration over an SiO$_2$ column (eluting with methylene chloride/methanol 98:2), evaporation of the eluate and recrystallisation from isopropanol, 1.8 g of crystals are obtained, m.p. 128°–130° C., [α]$_D$$^{20}$=−20.9° (1%, methanol)

The optical purity of the title compound is determined by HPLC chromatography on a chiral polyamide column and is at least 99%.

¹H-NMR (CDCl₃): δ=7.45–6.97 (9H, m, aryl-H); 4.90 (2H, s, broad, CH₂-7ring), 4.56, 4.59 (2H, 2-AB-system, N-CH₂-aryl); 3.88–2.98 (5H, m, N—CH₂—CH₂CH₃; CH—C=O; thiophene-CH₂ 2); 2.70; 2.68 (3H, 2s, CH₃-triazole); 2.55–1.90 (2H, m, thiophene-CH₂-3); 1.52 (2H, m, N—CH₂CH₂CH₃).

EXAMPLE 3

(+/−)-3-(4-(Methoxybenzyl)methylaminocarbonyl)-5-(2-chlorophenyl)-10-methyl-7H-cyclopenta[4,5]thieno-[3,2-f] [1,2,4]triazolo-[4,3-a][1,4]diazepine

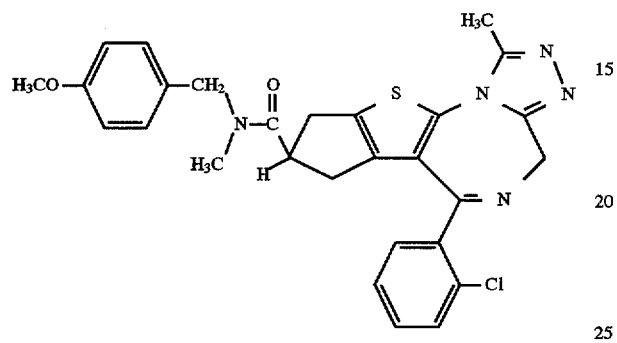

1.5 g (0.0038 mol) of racemic 3-carboxy-5-(2-chlorophenyl)-10-methyl-7H-cyclopenta[4,5]thieno[3,2-f]-[1,2,4]triazolo[4,3-a][1,4]diazepine are added to 0.5 g of thionyl chloride diluted with 50 ml of methylene chloride and the mixture is stirred for 2 hours at ambient temperature. Whilst cooling with ice, sufficient 4-methoxybenzylmethylamine is added to give a pH of 6. The mixture is stirred for 2 hours at ambient temperature, extracted twice with 20 ml of H₂O, the organic phase is dried, the solvent is distilled off and chromatographed over SiO₂. 1.6 g of the title compound are obtained.

¹H-NMR (DMSO-d6); δ=7.45–6.78 (8H, m, aryl-H); 4.80 (2H, AB-system, CH₂-7-ring); 4.39 (2H, s, N—CH₂-aryl); 3.87 (1H, m, CH—C=O); 3.75 (3H, s, OCH₃); 3.15 (2H, m, CH₂-2); 2.79 (3H, s, N—CH₃); 2.59 (3H, s, CH₃-triazole); 2.19 (2H, m, CH₂-4).

The compounds enumerated as follows may be obtained analogously:

EXAMPLE 4

S(−)-3-(Benzylaminocarbonyl)-5-(2-chlorophenyl)-10-methyl-7H-cyclopenta[4,5]thieno[3,2-f][1,2,4]triazolo-[4,3-a][1,4]diazepine

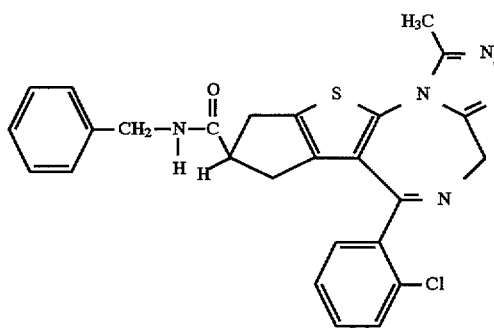

[α]_D=−37.4 (1%, methanol)

1H-NMR (CDCl₃): δ=7.47–7.14 (9H, m, aryl-H); 5.89 (1H, 7, J=5 Hz, NH); 4.88 (2H, s, broad, CH₂-7-ring), 4.40 (2H, m CH₂-aryl); 3.43–3.09 (3H, m, O=C—CH—CH₂); 2.68 (3H, s, CH₃-triazole); 2.50–2.06c(2H, m, CH₂-4-5-ring).

EXAMPLE 5

S(−)-3-(Benzylmethylaminocarbonyl-5-(2-chlorophenyl)-10-methyl-7H-cyclopenta[4,5]thieno[3,2-f][1,2,4]triazolo-[4,3-a][1,4]diazepine

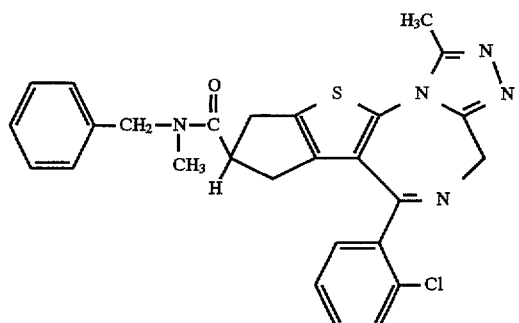

[α]_D=−31.4 (1%, methanol); m.p.: 202–204° C.

¹H-NMR (DMSO-d6): δ=7.47–7.06 (9H, m, aryl-H); 4.80 (2H, AB-system, CH₂-7-ring), 4.47 (2H, s, N—CH₂); 3.87 (1H, m, CH—C=O); 3.17 (2H, m, CH₂-2); 2.83 (3H, s, N—CH₃); 2.59 (3H, s, CH₃-triazole); 2.20 (2H, m, CH₂-4).

EXAMPLE 6

S(−)-3-(Benzylethylaminocarbonyl)-5-(2-chlorophenyl)-10-methyl-7H-cyclopenta[4,5]thieno[3,2-f][1,2,4]triazolo-[4,3-a][1,4]diazepine

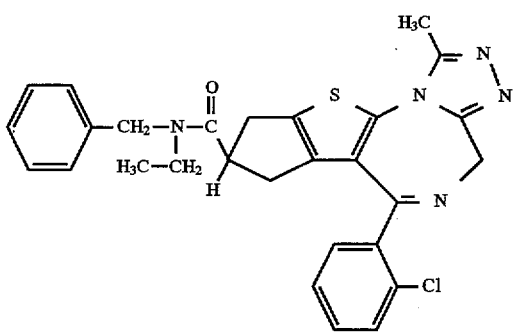

[α]_D=−27.6° C. (1%, methanol), m.p.: 204–205° C.

¹H-NMR (CDCl₃): δ=7.47–7.00 (9H, m, aryl-H); 4.89 (2H, s, broad, CH₂-7-ring), 4.56; 4.47 (2H, 2 AB-system, NCH₂-aryl); 3.87–2.93 (5H, m, N—CH₂—CH₃, NCOCH—CH₂(2)); 2.70; 2.68 (3H, 2s, CH₃-triazole); 2.57–2.00 (2H, m, CH₂(4)); 1.07 (3H, t, J=6 Hz, N—CH₂—CH₃).

EXAMPLE 7

S(−)-3-(Benzylbutylaminocarbonyl)-5-(2-chlorophenyl)-10-methyl-7H-cyclopenta[4,5]thieno-[3,2-f][1,2,4]triazolo-[4,3-a][1,4]diazepine

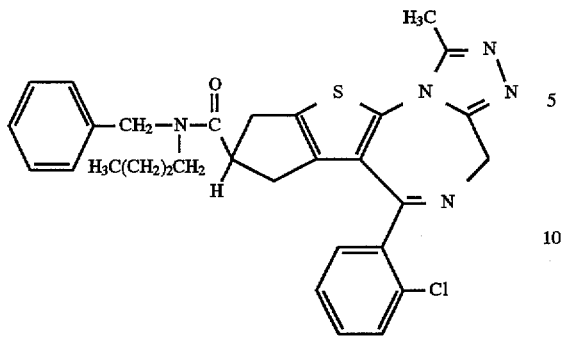

[α]$_D$ = −24.5° C. (1%, methanol)

¹NMR (CDCl$_3$): δ=7.47–7.01 (9H, m, aryl-H); 4.89 (2H, s, broad, CH$_2$-7-ring), 4.56; 4.49 (2H, 2 AB-system, N—CH$_2$-aryl); 3.88–2.93 (5H, m, N—CH$_2$(CH$_2$)$_2$—CH$_3$); O=C—CH—CH$_2$(2)); 2.70; 2.68 (3H, 2s, CH$_3$-triazole); 2.54–2.01 (2H, m, CH$_2$(4); 1.60–1.13 (4H, m, N—CH$_2$CH$_2$CH$_2$CH$_3$); 0.88 (3H, t, J=7 Hz, N—(CH$_2$)$_3$—CH$_3$).

EXAMPLE 8

S(−)-3-(Benzylisopropylaminocarbonyl)-5-(2-chlorophenyl)-10-methyl-7H-cyclopenta[4,5]thieno-[3,2-f][1,2,4]triazolo-[4,3-a][1,4]diazepine

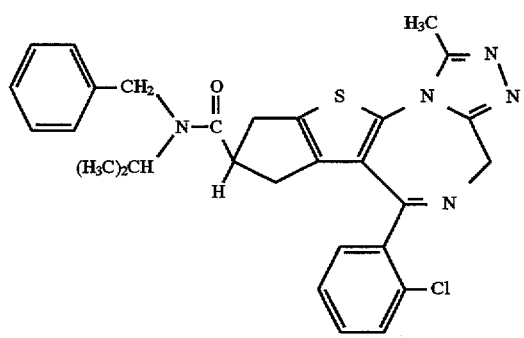

[α]$_D$ = −17.5° C. (1%, methanol)

¹H-NMR (CDCl$_3$): δ=7.47–7.06 (9H, m, aryl-H); 4.87 (2H, s, broad, CH$_2$-7-ring), 4.82 (1H, qu, J=6 Hz, N—CH); 4.47; 4.40 (2H, 2-AB-system), N—CH$_2$-aryl); 4.11–2.93 (3H, m, O=C—CH—CH$_2$(2)); 2.69; 2.67 (3H, 2s, CH$_3$-triazole); 2.50–1.79 (2H, m, CH$_2$(4)); 1.10 (4H, m, (CH$_3$(2)—CH—).

EXAMPLE 9

S(−)-3-(Benzylcyclopropylaminocarbonyl)-5-(2-chlorophenyl)-10-methyl-7H-cyclopenta[4,5]thieno-[3,2-f][1,2,4]triazolo-[4,3-a][1,4]diazepine

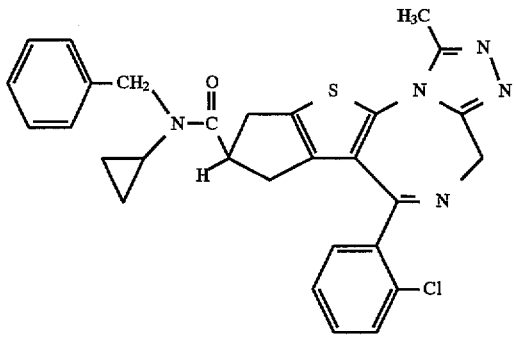

[α]$_D$ = −27.8 (1%, methanol)

¹H-NMR (CDCl$_3$): δ=7.46–7.02 (9H, m, aryl-H); 4.90 (2H, s, broad, CH$_2$-7-ring), 4.56 (2H, AB-system, N—CH$_2$-aryl); 4.26 (1H, m, O=C—CH); 3.24 (2H, m, CH$_2$(2)); 2.70 (3H, s, CH$_3$-triazole); 2.51–2.03 (3H, m, CH$_2$(4)); 0.93–0.62 (4H, m, (CH$_2$—CH$_2$ cyclopropane).

EXAMPLE 10

S(−)-3-(Dibenzylaminocarbonyl)-5-(2-chlorophenyl)-10-methyl-7H-cyclopenta[4,5]thieno-[3,2-f][1,2,4]-triazolo-[4,3-a][1,4]diazepine

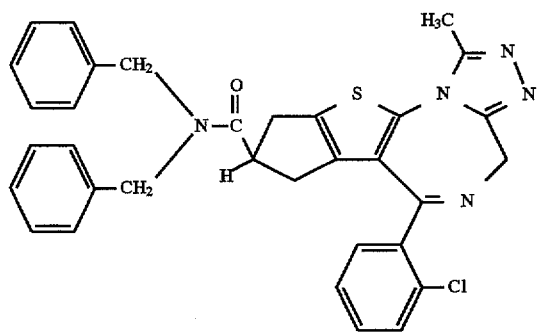

[α]$_D$ = −27.8° (1%, methanol)

¹-NMR (CDCl$_3$): δ=7.45–6.96 (14H, m, aryl-H); 4.89 (2H, s, broad, CH$_2$-7-ring), 4.57; 4.39 (4H, 2-AB-system, N—(CH$_2$(2)); 3.88–2.99 (3H, m, O=C—CH—CH$_2$(2)); 2.69 (3H, s, CH$_3$-triazole); 2.58–1.98 (2H, m, CH$_2$(4)).

EXAMPLE 11

S(−)-3-(Benzylallylaminocarbonyl)-5-(2-chlorophenyl)-10-methyl-7H-cyclopenta[4,5]thieno[3,2-f][1,2,4]-triazolo-[4,3-a][1,4]diazepine

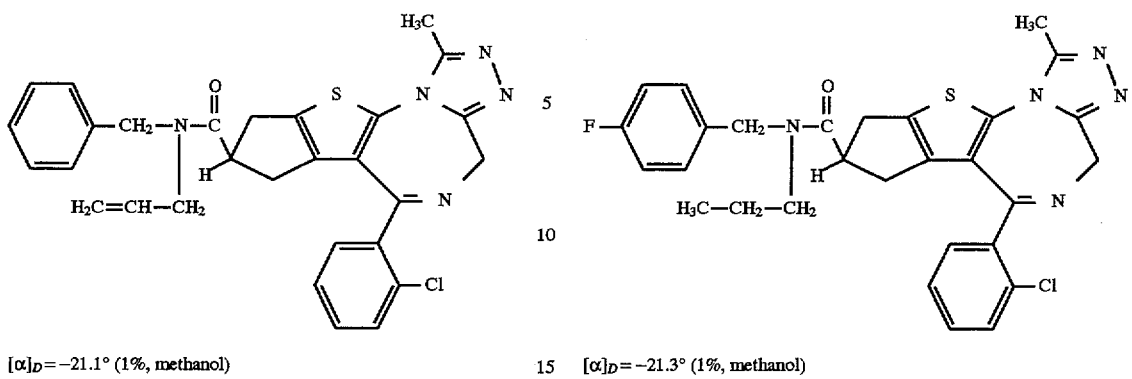

[α]$_D$ = −21.1° (1%, methanol)

[α]$_D$ = −21.3° (1%, methanol)

¹H-NMR (DMSO-d6): δ=7.45–7.05 (9H, m, aryl-H); 5.65 (1H, m, H=C); 5.03 (2H, m, =CH₂); 4.80 (2H, AB-system, CH₂-7-ring); 4.46 (2H, AB-system, N—CH₂-aryl); 4.84 (3H, m, O=C—CH, N—CH₂—CH=); 3.15 (2H, m, CH₂ (2)); 2.59 (3H, s, CH₃-triazole); 2.18 (2H, m, CH₂(4)).

¹H-NMR (CDCl₃): δ=7.45–6.88 (8H, m, aryl-H); 4.89 (2H, s, broad, CH₂-7-ring), 4.51, 4.45 (2H, 2-AB-system, N—CH₂-aryl); 3.86–2.92 (5H, m, N—CH₂CH₂CH₃, O=C—CH—CH₂(2)); 2.70; 2.68 (3H, 2s, CH₃-triazole); 2.51–2.03 (2H, m, CH₂(4)); 1.50 (2H, m, N—CH₂CH₂CH₃); 0.85 (3H, m, N—CH₂CH₂—CH₃).

EXAMPLE 12

(+/−)-3-(Benzylpropargylaminocarbonyl)-5-(2-chlorophenyl)-10-methyl-7H-cyclopenta[4,5]thieno-[3,2-f] [1,2,4]-triazolo-[4,3-a][1,4]diazepine

EXAMPLE 14

S (−)-3-((4-Chlorobenzyl)propylaminocarbonyl)-5-(2-chlorophenyl)-10-methyl-7H-cyclopenta[4,5]thieno-[3,2-f] [1,2,4]-triazolo-[4,3-a][1,4]diazepine

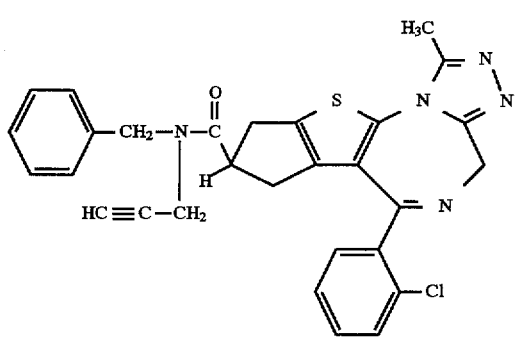

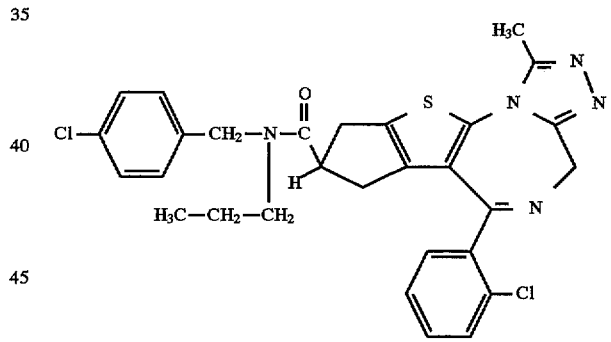

[α]$_D$ = −21.1° (1%, methanol)

¹H-NMR (CDCl₃): δ=7.46–7.00 (9H, m, aryl-H); 4.87 (2H, s, broad, CH₂-7-ring), 4.19 (2H, AB-system, N—CH₂—C≡); 4.62; 4.64 (2H, AB-system, N—CH₂-aryl); 3.75–2.98 (3H, m, O=C—CH—CH₂(2)); 2.70; 2.68 (3H, 2s, CH₃-triazole); 2.62–1.92 (2H, m, CH₂(4)); 2.26; 2.21 (1H, 2t, J=1 Hz, HC≡C).

¹H-NMR (DMSO-d6): δ=7.46–7.03 (8H, m, aryl-H); 4.80 (2H, AB-system, N—CH₂-7-ring); 4.46 (2H, AB-system, N—CH₂-aryl); 3.83 (1H, m, O=C—CH); 3.17 (4H, m, N—CH₂CH₂—CH₃; CH₂(2)); 2.59 (3H, s, CH₃-triazole); 2.15 (2H, m, CH₂(4)); 1.43 (2H, m, N—CH₂—CH₂CH₃); 0.77 (3H, m, N—CH₂CH₂CH₂).

EXAMPLE 13

S(−)-3-((4-Fluorobenzyl)propylaminocarbonyl)-5-(2-chlorophenyl)-10-methyl-7H-cyclopenta[4,5]thieno-[3,2-f] [1,2,4]-triazolo-[4,3-a][1,4]diazepine

EXAMPLE 15

S(−)-3-((4-Methylbenzyl)aminocarbonyl)-5-(2-chlorophenyl)-10-methyl- 7H-cyclopenta[4,5]thieno-[3,2-f] [1,2,4]-triazolo-[4,3-a][1,4]diazepine

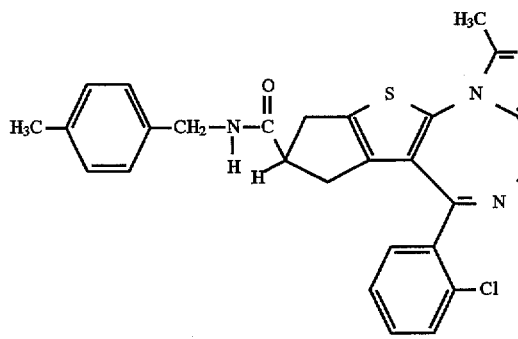

[α]$_D$ = −35.6° (1%, methanol)

¹H-NMR (CDCl₃): δ=7.45–7.03 (8H, m, aryl-H); 6.24 (1H, t, J=6 Hz, NH); 4.82 (2H, s, broad, CH₂-7-ring), 4.34 (2H, C.CH₂-aryl); 3.44–3.07 (3H, m, O=C—CH—CH₂(2)); 2.64 (3H, s, CH₃-triazole); 2.33 (3H, s, CH₃-aryl); 2.50–2.02 (2H, m, CH₂(4)).

EXAMPLE 16

S(−)-3-((4-Methylbenzyl)methylaminocarbonyl)-5-(2-chlorophenyl)-10-methyl-7H-cyclopenta[4,5]thieno-[3,2-f][1,2,4]-triazolo-[4,3-a][1,4]diazepine

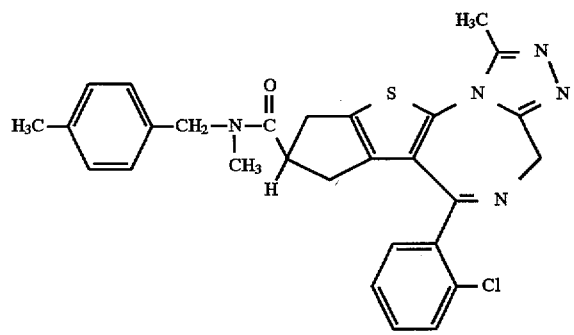

[α]$_D$ = −31.4° (1%, methanol)

¹H-NMR (CDCl₃): δ=7.45–6.89 (8H, m, aryl-H); 4.87 (2H, s, broad, CH₂-7-ring); 7.51, 4.44 (2H, 2AB-system, N—CH₂-aryl); 3.88–2.93 (3H, m, O=CH—CH₂(2)); 2.93, 2.87 (3H, 2s, N—CH₃); 2.70, 2.68 (3H, 2s, CH₃-triazole); 2.37, 2.34 (2H, 2s, CH₃-aryl); 2.55–2.02 (2H, m, CH₂(4)).

EXAMPLE 17

S(−)-3-((4-Trifluoromethylbenzyl)methylaminocarbonyl)-5-(2-chlorophenyl)-10-methyl-7H-cyclopenta[4,5]thieno-[3,2-f][1,2,4]-triazolo-[4,3-a][1,4]diazepine

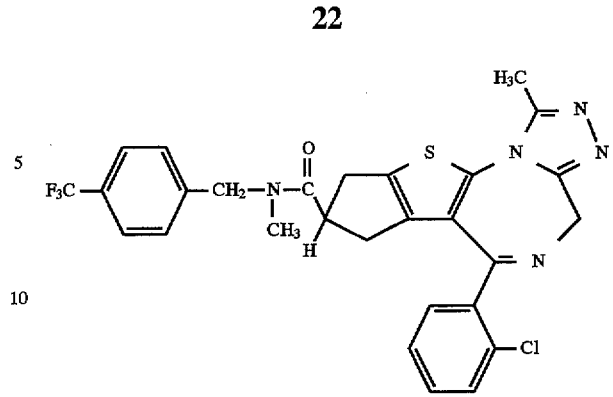

[α]$_D$ = −33.0° (1%, methanol).

¹H-NMR (CDCl₃): δ=7.66–7.14 (8H, m, aryl-H); 4.91 (2H, s, CH₂-7-ring); 4.59, 4.61 (2H, 2AB-system, N—CH₂-aryl); 3.89–2.92 (3H, m, OC—CH—CH₂(2)); 2.95, 2.89 (3H, 2s, N,CH₃); 2.70, 2.68 (3H, 2s, CH₃-triazole); 2.56–2.04 (2H, m, CH₂(4)).

EXAMPLE 18

S(−)-3-((4-Trifluoromethylbenzyl)propylaminocarbonyl)-5-(2-chlorophenyl)-10-methyl-7H-cyclopenta[4,5]thieno-[3,2-f][1,2,4]-triazolo-[triazolo-[4,3-a][1,4]diazepine

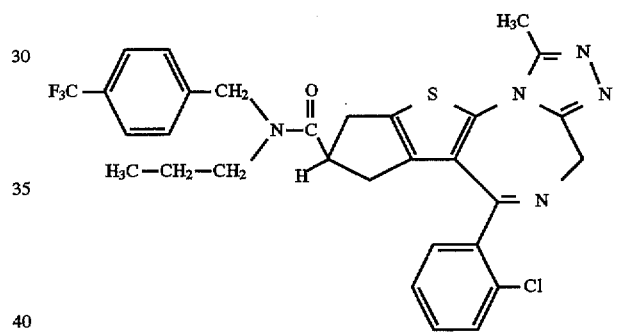

53 g (0.109 ml) of the S(−)-3-carboxy-5-(2-chlorophenyl)-10-methyl-7H-cyclopenta[4,5]thieno-[3,2-f][1,2,4]-triazolo-[4,3-a][1,4]diazepine are placed in 250 ml of DMF.

Then, at 20° C., 18.3 g (0.12 mol) of hydroxybenzotriazole (HOBT), 23.7 g (0.109 mol) of N-4-trifluoromethylbenzyl-N-n-propylamine and 25.6 g (0.125 mol) of dicyclohexyl-carbodiimide (DCCI) and a further 250 ml of dimethylformamide (DMF) were added. The mixture was left to react for 24 hours. It was then cooled to 5° C. and filtered. 500 ml of water were added to the filtrate and it was extracted with ethyl acetate. The combined organic phases were washed with water and saturated sodium hydrogen carbonate solution, dried with magnesium sulphate and filtered over kieselguhr/char-coal. After working up in the usual way, 50 g of colourless crystals of the title compound are obtained by crystallisation from ethanol/diisopropylether (1:1). The ³H-PAF-receptor bonding—determined using human thrombocytes—is K$_i$=1.8 nMol/liter. (The method used is described for example in European Patent Application 368 175).

[α]$_D$=−26.3° (1%, methanol); m.p. 144° C.

¹H-NMR (CDCl₃): δ=7.64–7.14 (8H, m, aryl-H); 4.87 (2H, s, broad, CH₂-7-ring); 4.61, 4.55 (2H, 2AB-system, n-CH₂-aryl); 3.90–2.95 (5H, m, OC—CH—CH₂, N—CH₂—CH₂—CH₃); 2.69, 2.67 (3H, 2s, CH₃-triazole):

2.50–1.93 (2H, m, CH₂(4)); 1.52 (2H, m, N—CH₂—CH₂—CH₃); 0.85 (3H, m, N—CH₂—CH₂—CH₃).

The synthesis of the carboxylic acid mentioned as starting compound is known from the prior art, e.g. European Patent Application 388 789.

EXAMPLE 18a (+/−)-3-((4-Trifluoromethylbenzyl)propylaminocarbonyl)-5-(2-chlorophenyl-10-methyl-7H-cyclopenta[4,5]thieno-[3,2-f][1,2,4]-triazolo-[4,3-a][1,4]diazepine Analogously to Example 18, the title compound is obtained, in the form of an amorphous white powder, from the racemic 3-carboxy-5-(2-chlorophenyl)-10-methyl-7H-cyclopenta[4,5]thieno[3,2-f][1,2,4]triazolo-[4,3-a]-[1,4]diazepine and N-4-trifluoromethylbenzyl-N-n-propylamine.

EXAMPLE 18b

R(+)-3-((4-Trifluoromethylbenzyl)propylaminocarbonyl)-5-(2-chlorophenyl)-10-methyl-7H-cyclopenta[4,5]thieno-[3,2-f][1,2,4]-triazolo-[4,3-a][1,4]diazepine The title compound is obtainable from the corresponding R(+)-carboxylic acid analogously to Example 18.

$[\alpha]_D$=+26° (1%, methanol).

EXAMPLE 19

S(−)-3-((4-Methylsulphonylbenzyl)propylaminocarbonyl)-5-(2-chlorophenyl)-10-methyl-7H-cyclopenta[4,5]thieno-[3,2-f][1,2,4]-triazolo-[4,3-a][1,4]diazepine

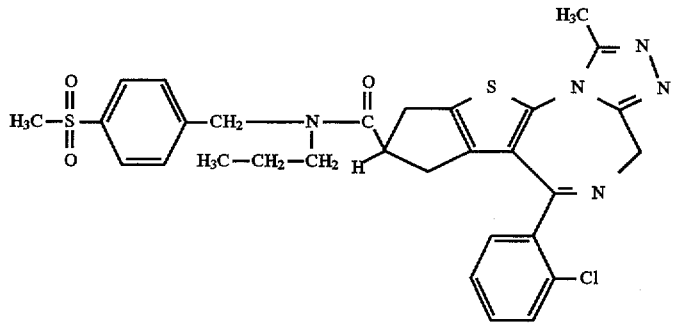

¹H-NMR (CDCl₃): δ=7.95–7.21 (8H, m, aryl-H); 4.92 (2H, s, broad, CH₂-7-ring); 4.63, 4.57 (2H, 2AB-system, N—CH₂-aryl; 3.92–2.98 (5H, m, O=C—CH—CH₂(2), N—CH₂—CH₂—CH₃); 3.07, 3.05 (3H, 2s, SO₂CH₃); 2.70, 2.68 (3H, 2s, CH₃-triazole); 2.54–2.10 (2H, m, CH₂(4)); 1.52 (2H, m, N—CH₂—CH₂—CH₃); 0.85 (3H, m, N—CH₂—CH₂—CH₃).

EXAMPLE 20

(+/−)-3-((2-Hydroxybenzyl)propylaminocarbonyl)-5-(2-chlorophenyl)-10-methyl-7H-cyclopenta[4,5]thieno-[3,2-f][1,2,4]-triazolo-[4,3-a][1,4]diazepine

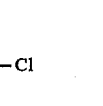

¹H-NMR (CDCl₃): δ=5.47–6.74 (8H, m, aryl-H); 4.88 (2H, s, broad, CH₂-7-ring); 4.42 (2H, AB-system, N—CH₂-aryl); 3.73–3.01 (5H, m, O=C—CH₂(2), N—CH₂—CH₂—CH₃); 2.46 (3H, s, CH₃-triazole); 2.50–1.96 (2H, m, CH₂(4), 1.58 (2H, m, N—CH₂—CH₂—CH₃); 0.90 (3H, m, N—CH₂—CH₂—CH₃); 9.40 (1H, s, OH).

EXAMPLE 21

(+/−)-3-(Phenethylpropylaminocarbonyl)-5-(2-chlorophenyl)-10-methyl-7H-cyclopenta[4,5]thieno-[3,2-f][1,2,4]-triazolo-[4,3-a][1,4]diazepine

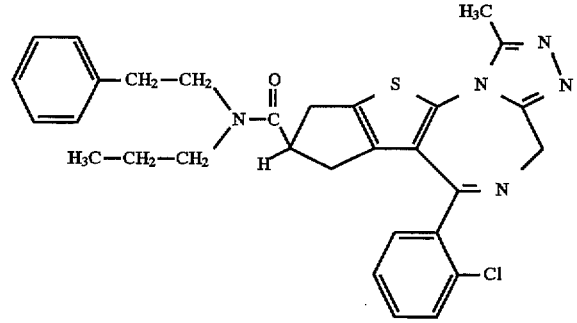

¹H-NMR (CDCl₃): δ=7.47–6.99 (9H, m, aryl-H); 4.84 (2H, s, broad, CH₂-7-ring); 3.67–2.73 (9H, m, N—CH₂—CH₂-aryl, N—CH₂—CH₂—CH₃, O=C—CH—CH₂(2)); 2.69, 2.68 (3H, 2s, CH₃-triazole); 2.46–1.83 (2H, m, CH₂(4)); 1.50 (2H, m, N—CH₂—CH₂—CH₃); 0.85 (3H, m, N—CH₂—CH₂—CH₃).

EXAMPLE 22

S(−)-3-((2-Furfurylmethyl)propylaminocarbonyl)-5-(2-chlorophenyl)-10-methyl-7H-cyclopenta[4,5]thieno-[3,2-f][1,2,4]-triazolo-[4,3-a][1,4]diazepine

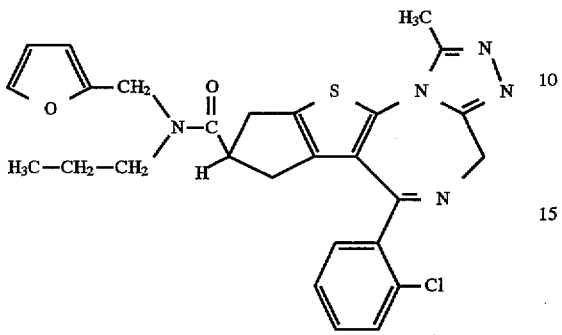

[α]$_D$ = −14.5° (1%, methanol)

$^1$H-NMR (CDCl$_3$): δ=7.46–6.11 (7H, m, aryl-H, furan-H); 4.88 (2H, s, broad, CH$_2$-7-ring); 4.52, 4.37 (2H, 2AB-system, N-CH$_2$-furan); 3.90–3.05 (5H, m, O=C—CH—CH$_2$(2), N—CH$_2$—CH$_2$—CH$_3$); 2.69 (3H, s, CH$_3$-triazole); 2.55–1.96 (2H, m, CH$_2$(4)); 1.46 (2H, m, N—CH$_2$—CH$_2$—CH$_3$); 0.83 (3H, m, N—CH$_2$—CH$_2$—CH$_3$).

EXAMPLE 23

S(−)-3-((2-Thienylmethyl)propylaminocarbonyl)-5-(2-chlorophenyl)-10-methyl-7H-cyclopenta[4,5]thieno-[3,2-f][1,2,4]-triazolo-[4,3-a][1,4]diazepine

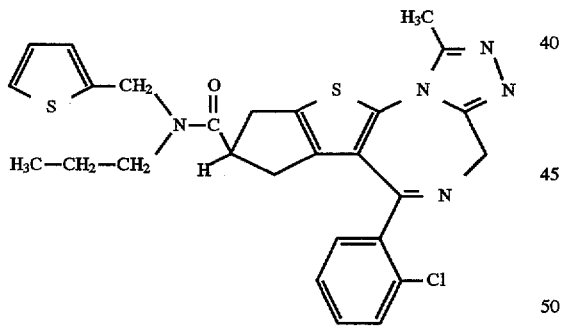

$^1$H-NMR (CDCl$_3$): δ=7.43–6.78 (7H, m, aryl-H, thiophene-H); 4.89 (2H, s, broad, CH$_2$-7-ring); 4.67, 4.59 (2H, 2AB-system, N—CH$_2$-thiophene); 3.74–3.14 (5H, m, O=C—CH—CH$_2$(2), N—CH$_2$—CH$_2$—CH$_3$); 2.70 (3H, s, CH$_3$-triazole); 2.57–1.95 (2H, m, CH$_2$(4)); 1.52 (2H, m, N—CH$_2$—CH$_2$—CH$_3$); 0.86 (3H, m, N—CH$_2$—CH$_3$).

EXAMPLE 24

R(+)-3-((4-Trifluoromethylbenzyl)methylaminocarbonyl)-5-(2-chlorophenyl)-10-methyl-7H-cyclopenta[4,5]thieno-[3,2-f][1,2,4]-triazolo-[4,3-a][1,4]diazepine

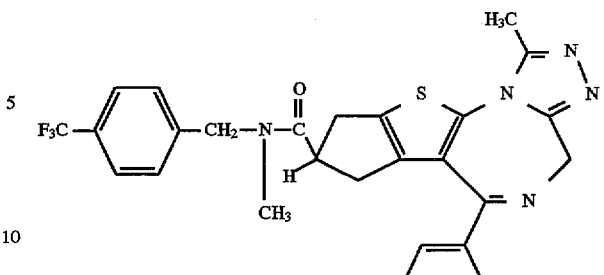

[α]$_D$ = +30.2° (1%, methanol)

$^1$H-NMR (CDCl$_3$): δ=7.65–7.09 (8H, m, aryl-H); 4.88 (2H, s, broad, CH$_2$-7-ring); 4.61, 4.56 (2H, 2AB-system, N—CH$_2$-aryl); 3.90–2.98 (3H, m, O=C—CH—CH$_2$(2)); 2.95, 2.90 (3H, 2s, N—CH$_3$); 2.70, 2.68 (3H, 2s, CH$_3$-triazole); 2.54–2.07 (2H, m, CH$_2$(4)).

EXAMPLE 25

(+/−)-3-(Benzylmethylaminocarbonyl)-5-(2-chlorophenyl)-10-methyl-7H-cyclopenta[4,5]thieno-[3,2-f][1,2,4]-triazolo-[4,3-a][1,4]diazepine

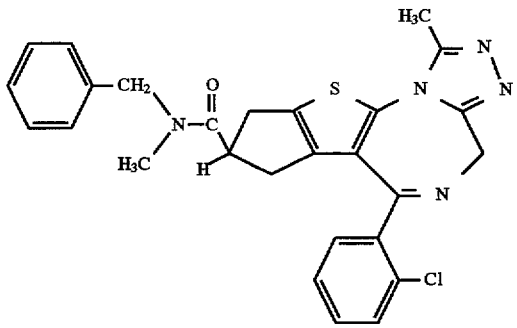

$^1$H-NMR (CDCl$_3$): δ=7.47–7.00 (9H, m, aryl-H); 4.92 (2H, s, broad, CH$_2$-7-ring); 4.56, 4.50 (2H, 2AB-system, N—CH$_2$-aryl); 3.88–2.93 (3H, m, O=C—CH—CH$_2$(2)); 2.94, 2.86 (3H, 2s, N—CH$_3$); 2.71, 2.69 (3H, 2s, CH$_3$-triazole); 2.55–2.02 (2H, m, CH$_2$(4)).

EXAMPLE 26

(+/−)-3-(Benzylpropylaminocarbonyl)-5-(2-chlorophenyl)-10-methyl-7H-cyclopenta[4,5]thieno-[3,2-f][1,2,4]-triazolo-[4,3-a][1,4]diazepine

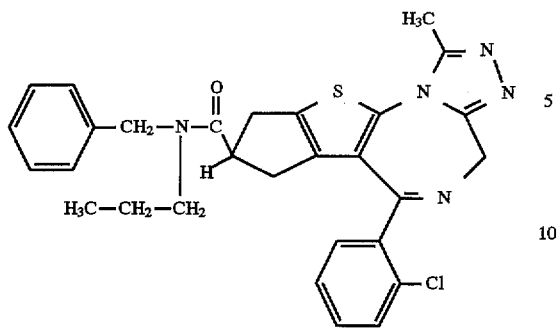
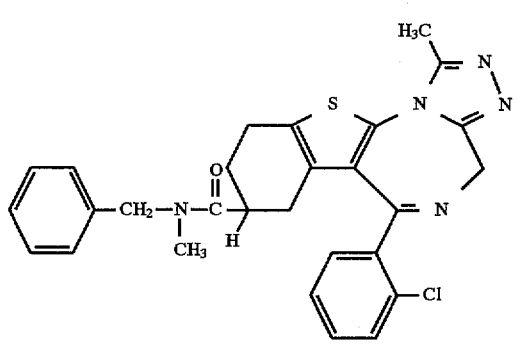

¹H-NMR (CDCl₃): δ7.47–7.00 (9H, m, aryl-H); 4.90 (2H, s, broad, CH₂-7-ring); 4.56, 4.47 (2H, 2AB-system, N—CH₂-aryl); 3.88–2.93 (5H, m, O=C—CH—CH₂(2), N—CH₂—CH₂—CH₃); 2.70, 2.68 (3H, 2s, CH₃-triazole); 2.57–1.80 (2H, m, CH₂(4)); 1.52 (2H, m, N—CH₂—CH₂—C₃); 0.85 (3H, m, N—CH₂—CH₂—CH₃).

EXAMPLE 27

(+/−)-3-(Benzylmethylaminocarbonyl)-5-(2-chlorophenyl)-7H-cyclopenta[4,5]thieno-[3,2-f][1,3]-imidazolo[1,2-a][1,4]diazepine

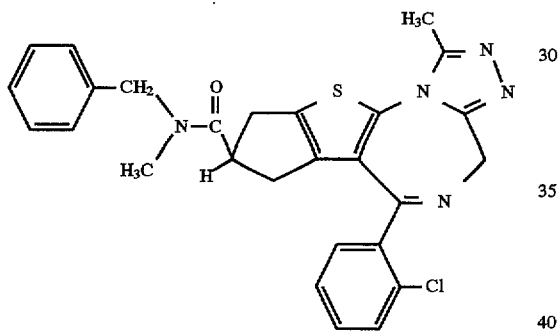

¹H-NMR (DMSO-d6); δ=7.45–7.00 (11H, m, aryl-H, imidazole-H); 4.70 (2H, AB-system, CH₂-7-ring); 4.46 (2H, s, N—CH₂-aryl); 2.81 (3H, s, N—CH₃); 3.83 (1H, m, O=C—CH); 3.12 (2H, m, CH₂(2)); 2.15 (2H, m, CH₂(4)).

EXAMPLE 28

(+/−)-4-(Benzylmethylaminocarbonyl)-6-(2-chlorophenyl)-2,3,4,5-tetrahydro-8H-[1]benzothieno[3,2-f]-[1,3]imidazo[1,2-a][1,4]-diazepine ¹H-NMR (DMSO-d6): δ=7.45–7.02 (9H, m, aryl-H); 6.78 (1H, qu, J=0.5 Hz, HC); 4.42 (2H, AB-system, N—CH₂-aryl); 4.68 (2H, s, broad, CH₂-7-ring); 2.93–2.69 (3H, m, O=C—CH, CH₂(2)); 2.38 (3H, d, J=0.5 Hz, CH₃-imidazole); 2.07–1.67 (4H, m, CH₂(3), CH₂(5)).

M.p.: 159°–160° C.

EXAMPLE 29

(+/−)-3-(4-(4-Trifluoromethylphenyl)-ethano)-benzylpropylaminocarbonyl)-5-(2-chlorophenyl)-10-methyl-7H-cyclopenta-[4,5]thieno-[3,2-f][1,2,4]-triazolo-[4,3-a][1,4]diazepine

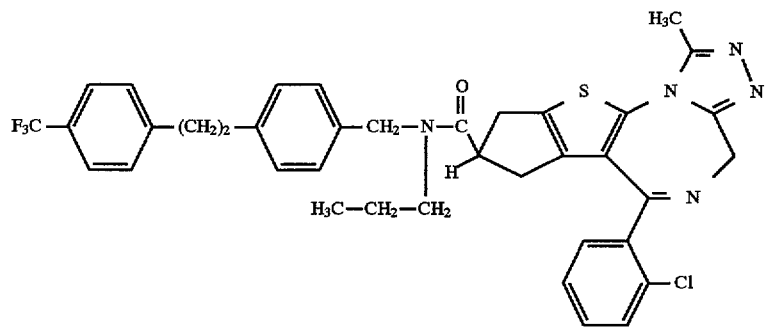

¹H-NMR (DMSO-d6): δ=7.62–6.95 (12H, m, aryl-H); 4.47 (2H, AB-system, N—CH₂-aryl); 4.41 (1H, m, CH-7-ring); 3.83 (1H, m, O=C—CH); 3.28–2.40 (10H, m, aryl-CH₂—CH₂), N—CH₂—CH₂—CH₃, CH₂(2), CH₂(4)); 1.40 (2H, m, N—CH₂—CH₂—CH₃); 1.89 (3H, d, J=6 Hz, CH—CH₃); 0.74 (3H, m, N—CH₂—CH₂—CH₃).

EXAMPLE 30

(+/−)-3-(4-(2-(3,4,5-Trimethoxyphenyl)ethano)benzyl-aminocarbonyl)-5-(2-chlorophenyl)-10-methyl-7H-cyclopenta[4,5]thieno-[3,2-f][1,2,4]-triazolo-[4,3-a]-[1,4]diazepine

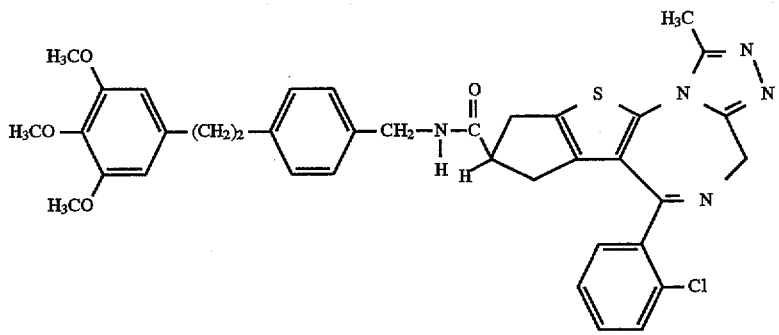

EXAMPLE 31

3-((4-Hydroxyphenethyl)aminocarbonyl)-5-(2-chlorophenyl)-10-methyl-7H-cyclopenta[4,5]thieno-[3,2-f][1,2,4]triazolo-[4,3-a][1,4]diazepine

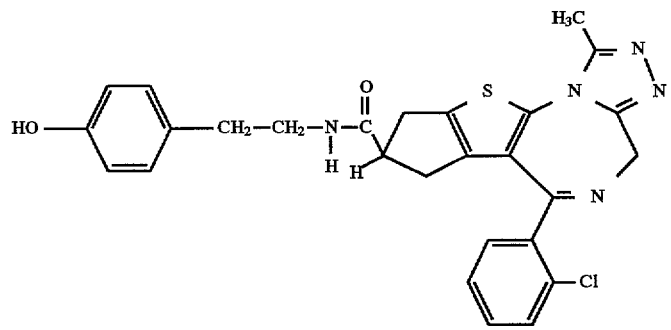

¹H-NMR (DMSO-d6): δ=7.93 (1H, t, J=7 Hz, NH); 7.52–6.59 (8H, m, aryl-H); 9.26 (1H, s, OH); 3.61–2.93 (7H, m, O=C—CH—CH₂(2), N—CH₂—CH₂); 4.76 (2H, s, broad, CH₂-7-ring); 2.61 (3H, s, CH₃-triazole); 2.09 (2H, m, CH₂(4)).

EXAMPLE 32

4-(2-Chlorophenyl)-9-methyl-thieno-[3,2-f][1,2,4]-triazolo-[4,3-a][1,4]diazepino-2-(2-ethano)-carboxylic acid (4-fluorobenzyl)propylamide

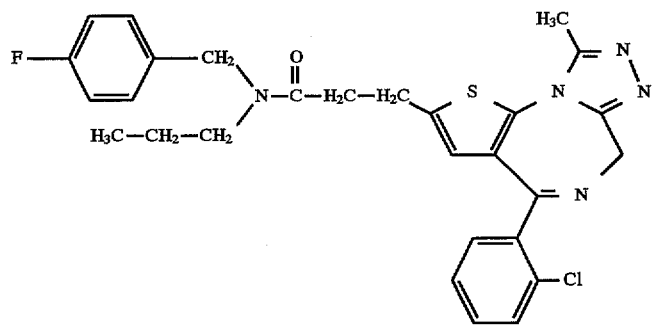

¹H-NMR (CDCl₃): δ=7.45–6.89 (8H, m, aryl-H); 6.43, 6.37 (1H, 2s, thiophene-H); 4.92 (2H, s, CH₂-7-ring); 4.53, 4.45 (2H, 2s, N—CH₂-aryl); 3.39–2.55 (6H, m, O=C—CH₂—CH₂—CH₃); 2.69 (3H, s, CH₃-triazole); 1.52 (2H, m, N—CH₂—CH₂—CH₃); 0.86 (3H, m, N—CH₂—CH₂—CH₃).

M.p.: 176°–178° C.

EXAMPLE 33

4-(2-Chlorophenyl)-9-methyl-thieno-[3,2-f][1,2,4]-triazolo-[4,3-a][1,4]diazepino-2-(2-ethano)-carboxylic acid (4-trifluoromethylbenzyl)propylamide

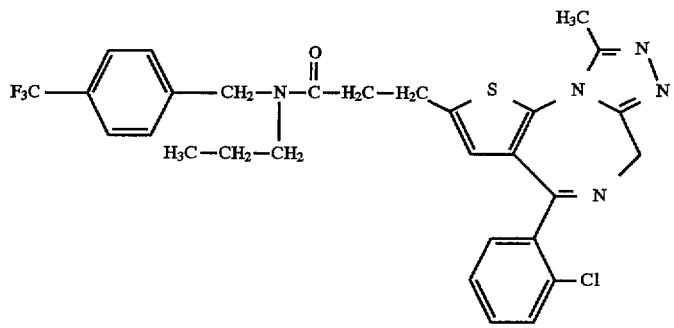

¹H-NMR (CDCl₃): δ=7.62–7.19 (8H, m, aryl-H); 6.45, 6.38 (1H, 2s, thiophene-H); 4.92 (2H, s, CH₂-7-ring); 4.63, 4.56 (2H, 2s, N—CH₂-aryl); 3.40–2.52 (6H, m, O=C—CH₂—CH₂, N—CH₂—CH₂—CH₃); 2.69 (3H, s, CH₃-triazole); 1.54 (2H, m, N—CH₂—CH₂—CH₃); 0.88 (3H, m, N—CH₂—CH₂—CH₃).

M.p.: 182°–183° C.

EXAMPLE 34

4-(2-Chlorophenyl)-9-methyl-thieno-[3,2-f][1,2,4]-triazolo-[4,3-a][1,4]diazepino-2-(2-ethano)-carboxylic acid (4-trifluoromethylbenzyl)methylamide

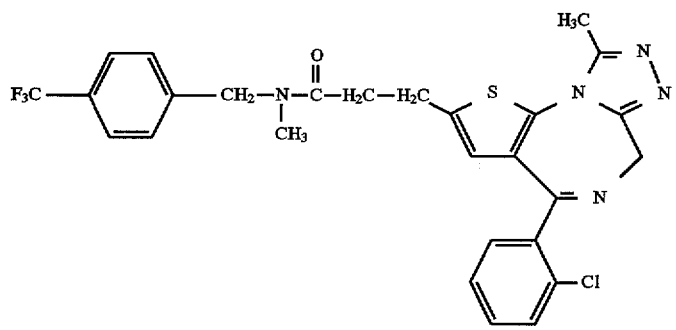

¹H-NMR (CDCl₃): δ=7.64–7.14 (8H, m, aryl-H); 6.46, 6.39 (1H, 2s, thiophene-H); 4.93 (2H, s, CH₂-7-ring); 4.64, 4.56 (2H, 2s, N—CH₂-aryl); 3.18 (2H, m, N—CH₂); 2.99, 2.93 (3H, 2s, N—CH₃); 2.73, 2.70 (3H, 2s, CH₃-triazole); 2.72 (2H, m, CH₂-thiophene).

EXAMPLE 35

4-(2-Chlorophenyl)-9-methyl-thieno-[3,2-f][1,2,4]-triazolo-[4,3-a][1,4]diazepino-2-(2-ethano)-carboxylic acid (4-methylsulphonylbenzyl)propylamide

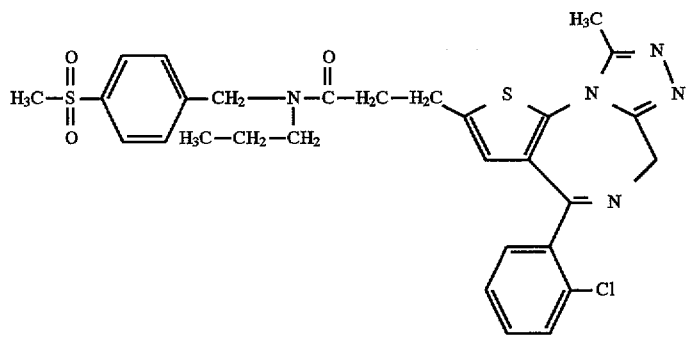

¹H-NMR (CDCl₃): δ=7.93–7.21 (8H, m, aryl-H); 6.45, 6.38 (1H, 2s, thiophene-H); 4.93 (2H, s, CH₂-7-ring); 4.67, 4.59 (2H, 2s, N—CH₂-aryl); 3.40–2.50 (6H, m, O═C—CH₂—CH₂, N—CH₂—CH₂—CH₃); 3.05, 5.02 (3H, 2s, SO₂—CH₃); 2.70 (3H, s, CH3-triazole); 1.54 (2H, m, N—CH₂—CH₂—CH₃); 0.87 (3H, m, N—CH₂—CH₂—CH₃).

M.p.: 172°–174° C.

EXAMPLE 36

4-(2-Chlorophenyl)-9-methyl-thieno-[3,2-f][1,2,4]-triazolo-[4,3-a][1,4]diazepino-2-(2-ethano)-carboxylic acid (4-(4-trifluoromethylphenyl)ethano)benzylpropyl-amide

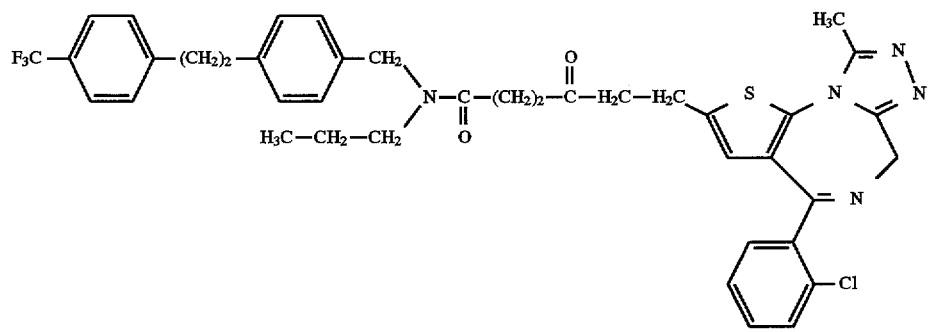

¹H-NMR (DMSO-d6): δ=7.57–7.08 (12H, m, aryl-H); 6.45 (1H, s, thiophene-H); 4.78 (2H, s, CH₂-7-ring); 4.45 (2H, s, N—CH₂-aryl); 3.17–2.66 (10H, m, O═C—CH₂—CH₂, N—CH₂CH₂—CH₃, aryl-CH₂—CH₂; 2.57 (3H, s, CH₃-triazole); 1.42 (2H, m, N—CH₂CH₂—CH₃); 0.76 (3H, m, N—CH₂—CH₂—CH₃).

EXAMPLE 37

(+/−)-3-Benzylpropylaminocarbonyl-5-(2-chlorophenyl)-7,10-dimethyl-7H-cyclopenta[4,5]thieno-[3,2-f][1,2,4]-triazolo-[4,3-a][1,4]diazepine

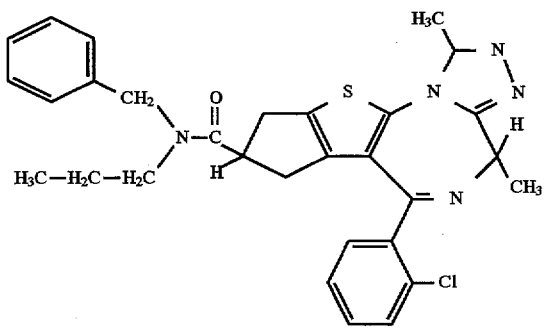

¹H-NMR (CDCl₃): δ=7.48–6.98 (9H, m, aryl-H); 4.54, 4.52 (2H, 2-AB-systems, N—CH₂-aryl); 4.38, 4.32 1H, 2 qu, J=7 Hz, N—CH—C═N); 3.86–2.98 (5H, m, N—CH₂CH₂CH₃; CH—C═O; thiophene-CH₂-2); 2.69, 2.67 (3H, 2s, CH₃-triazole); 2.55–1.90 (2H, m, thiophene-CH₂-3); 2.03, 1.85 (3H, 2d, J=7 Hz, CH₃-CH); 1.52 (2H, m, N—CH₂CH₂CH₃); 0.95 (3H, m, N—CH₂CH₂CH₃).

EXAMPLE 38

(+/−)-3-((4-Trifluoromethylbenzyl)propylaminocarbonyl)-5-(2-chlorophenyl)-7,10-dimethyl-7H-cyclopenta[4,5]-thieno-[3,2-f][1,2,4]triazolo[4,3-a][1,4]diazepine Starting from 3-carboxy-5-(2-chlorophenyl)-7,10-dimethyl-7H-cyclopenta-[4,5]thieno[3,2-f][1,2,4]-triazolo-[4,3-a][1,4]diazepine—obtainable from the corresponding 3-methoxycarbonyl compound (European Patent Application 368,175, particularly Example 9) by saponification—the title compound is obtained by reacting with N-4-trifluoromethylbenzyl-N-n- propylamine analogously to Example 18.

EXAMPLE 39

3-S(−)-((4-Trifluoromethylbenzyl)propylaminocarbonyl)-5-(2-chlorophenyl)- 7,10-dimethyl-7H-cyclopenta[4,5]-thieno [3,2-f][1,2,4]triazolo[4,3-a][1,4]diazepine Starting from S(−)-3-carboxy-5-chlorophenyl-7,10-dimethyl-7H-cyclopenta[4,5]thieno[3,2-f][1,2,4]-triazolo-[4,3-a][1,4]diazepine, the title compound is obtained analogously to Example 38.

The two enantiomers can be separated as in European Patent Application 368 175 using optically active columns.

The 3-S(−)-((4-trifluoromethylbenzyl)propylamino-benzyl)propylaminocarbonyl-5-(2-chlorophenyl-9-7S-7,10-dimethyl-7H-cyclopenta[4,5]thieno[3,2-f][1,2,4]-triazolo-[4,3-a][1,4]diazepine and the 3-S(−)-((4-Trifluoromethylbenzyl)propylaminocarbonyl-5-(2-chlorophenyl)-7R-7,10-dimethyl-7H-cyclopenta[4,5]-thieno[3,2-f][1,2,4]triazolo[4,3-a][1,4]diazepine are obtained.

EXAMPLE 40

(+/−)-3-((4-Trifluoromethylbenzyl)propylaminocarbonyl)-5-(2-chloropenta)-7,7,10-trimethyl-cyclopenta[4,5]-thieno [3,2-f][1,2,4]triazolo[4,3-e][1,4]diazepine.

Starting from 3-carboxy-5-(2-chlorophenyl-7,7,10-trimethyl-cyclopenta[4,5]thieno[3,2-f][1,2,4]-triazolo-[4,3-a][1,4]diazepine, the title compound is obtained analogously to Example 18.

The new compounds of general formula Ia may be administered to warm blooded animals by topical, oral, parenteral or transdermal route or by inhalation. The compounds are present as active ingredients in conventional preparations, e.g. in compositions consisting essentially of an inert pharmaceutical carrier and an effective dose of the active substance, such as plain or coated tablets, capsules, lozenges, powders, solutions, suspensions, aerosols for inhalation, ointments, emulsions, syrups, suppositories, etc. An effective dose of the compounds according to the invention for oral use is between 1 and 50, preferably between 3 and 20 mg/dose, or for intravenous or intramuscular use between 0.01 and 50, preferably between 0.1 and 10 mg/dose. For inhalation, solutions containing 0.01 to 1.0, preferably 0.1 to 0.5% of active substance should be used.

The following Examples serve to illustrate the invention.

EXAMPLE 1

Tablets containing 10 mg of substance of formula

| Composition: | |
|---|---|
| Substance of formula I | 10.0 mg |
| Corn starch | 57.0 mg |
| Lactose | 48.0 mg |
| Polyvinylpyrrolidone | 4.0 mg |
| Magnesium stearate | 1.0 mg |
| | 120.0 mg |

Method of preparation

The active substance, corn starch, lactose and polyvinylpyrrolidone are mixed together and moistened with water. The moist mixture is rubbed through a 1.5 mm mesh screen and dried at about 45° C. The dry granules are rubbed through a 1.0 mm mesh screen and mixed with magnesium stearate. The finished mixture is compressed in a tablet press using 7 mm diameter punches provided with a dividing notch, to form tablets. Weight of tablet: 120 mg

EXAMPLE 2

Coated tablets containing 5 mg of substance of formula I

| Composition: | |
|---|---|
| Substance B of formula I | 5.0 mg |
| Corn starch | 41.5 mg |
| Lactose | 30.0 mg |
| Polyvinylpyrrolidone | 3.0 mg |
| Magnesium stearate | 0.5 mg |
| | 80.0 mg |

Method of preparation

The active substance, corn starch, lactose and polyvinylpyrrolidone are thoroughly mixed and moistened with water. The moist mass is rubbed through a 1 mm mesh screen, dried at about 45° C. and the granules are then rubbed through the same screen. After the addition of magnesium stearate, convex tablet cores with a diameter of 6 mm are compressed in a tablet making machine. The tablet cores produced in this way are coated in known manner with a coating consisting essentially of sugar and talc. The finished coated tablets are polished with wax. Weight of coated tablet: 130 mg

EXAMPLE 3

Tablets containing 50 mg of substance of formula I

| Composition: | |
|---|---|
| Substance B of formula I | 50.0 mg |
| Calcium phosphate | 70.0 mg |
| Lactose | 40.0 mg |
| Corn starch | 35.0 mg |
| Polyvinylpyrrolidone | 3.5 mg |
| Magnesium stearate | 1.5 mg |
| | 200.0 mg |

Method of preparation

The substance, calcium phosphate, lactose and corn starch are uniformly moistened with an aqueous solution of polyvinylpyrrolidone. The mass is passed through a 2 mm mesh screen, dried in a circulating air dryer at 50° C. and screened once more. After the lubricant has been added the granules are compressed in a tablet making machine.

EXAMPLE 4

Capsules containing 50 mg of substance of formula I

| Composition: | |
|---|---|
| Substance of formula I | 50.0 mg |
| Corn starch | 268.5 mg |
| Magnesium stearate | 1.5 mg |
| | 320.0 mg |

Method of preparation

The substance and corn starch are mixed together and moistened with water. The moist mass is screened and dried. The dry granules are screened and mixed with magnesium stearate. The finished mixture is packed into size 1 hard gelatine capsules.

EXAMPLE 5

Suppositories containing 50 mg of substance of formula

| Composition: | |
|---|---|
| Substance of formula I | 50 mg |
| Solid fat | 1,650 mg |
| | 1,700 mg |

Method of preparation

The hard fat is melted. At 40° C. the ground active substance is homogeneously dispersed therein. It is cooled to 38° C. and poured into slightly chilled suppository moulds.

EXAMPLE 6

Oral suspension containing 50 mg of substance of formula I per 5 ml

| Composition: | |
|---|---|
| Substance of formula I | 50 mg |
| Hydroxyethylcellulose | 50 mg |
| Sorbic acid | 5 mg |
| 70% Sorbitol | 600 mg |
| Glycerol | 200 mg |
| Flavouring | 15 mg |
| Water to | 5 ml |

Method of preparation

Distilled water is heated to 70° C. Hydroxyethyl-cellulose is dissolved therein with stirring. After the addition of sorbitol solution and glycerol the mixture is cooled to ambient temperature. At ambient temperature, sorbic acid, flavouring and substance are added. The suspension is evacuated with stirring in order to eliminate air.

What is claimed is:

1. A thienodiazepine of the formula Ib:

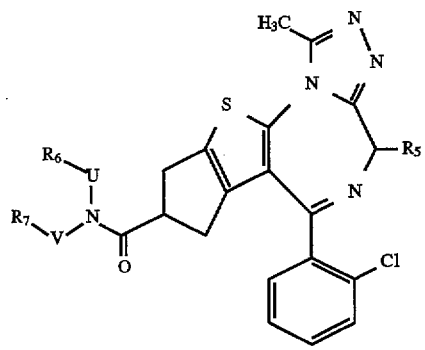

wherein

U is a single bond, branched or unbranched $C_{1-4}$-alkylene, $C_{3-4}$-alkenylene or $C_{3-4}$-alkynylene;

V is methylene or ethylene;

$R_5$ is hydrogen or methyl;

$R_6$ is hydrogen, cyclopropyl or a group of formula

wherein

K is hydrogen, $CF_3$ or halogen; and $\alpha$ is an integer selected from 1, 2, 3, 4 and 5

$R_7$ is a group of formula

wherein

L is hydrogen, F, Cl, Br, methyl, $CF_3$, $CH_3O_2S$, alkoxy or hydroxy; and $\beta$ is an integer selected from 1, 2, 3, 4, and 5, wherein if $\alpha$ or $\beta$ is greater than 1, all the Ks or Ls may be identical, partially identical or different.

2. The thienodiazepine:

s-(−)-3-((4-trifluoromethylbenzyl)propylaminocarbonyl)-5-(2-chlorophenyl)-10-methyl-7H-cyclopenta[4,5]thieno-[3,2-f][1,2,4]-triazolo-[4,3-a][1,4]-diazepine.

3. A pharmaceutical composition of matter comprising a compound as recited in claim 1 or 2 and a pharmaceutically acceptable carrier.

4. A method of treating diseases in a warm-blooded animal induced by endogenously formed PAF which comprises administering to said animal a therapeutically effective amount of a compound as recited in claim 1 or 2.

* * * * *